(12) United States Patent
Auld et al.

(10) Patent No.: US 7,189,226 B2
(45) Date of Patent: Mar. 13, 2007

(54) COAXIAL ILLUMINATED LASER ENDOSCOPIC PROBE AND ACTIVE NUMERICAL APERTURE CONTROL

(75) Inventors: Michael D. Auld, Chesterfield, MO (US); James C. Easley, St. Charles, MO (US); Jonathan S. Kane, Hudson, NH (US); Gregg Scheller, Wildwood, MO (US)

(73) Assignee: Synergetics, Inc., O'Fallon, MO (US)

( * ) Notice: Subject to any disclaimer, the term of this patent is extended or adjusted under 35 U.S.C. 154(b) by 13 days.

(21) Appl. No.: 10/900,939

(22) Filed: Jul. 27, 2004

(65) Prior Publication Data

US 2005/0033389 A1 Feb. 10, 2005

Related U.S. Application Data

(60) Provisional application No. 60/577,740, filed on Jun. 5, 2004, provisional application No. 60/577,618, filed on Jun. 5, 2004, provisional application No. 60/550,979, filed on Mar. 5, 2004, provisional application No. 60/490,399, filed on Jul. 28, 2003.

(51) Int. Cl.
*A61B 18/22* (2006.01)

(52) U.S. Cl. ............................. 606/11; 606/13; 600/108

(58) Field of Classification Search ................ 606/4–6, 606/10–16; 600/108
See application file for complete search history.

(56) References Cited

U.S. PATENT DOCUMENTS

| | | | | |
|---|---|---|---|---|
| 2,131,852 A | * | 10/1938 | Brackett | 362/268 |
| 4,447,121 A | * | 5/1984 | Cooper et al. | 385/87 |
| 4,483,585 A | * | 11/1984 | Takami | 385/115 |
| 4,878,725 A | * | 11/1989 | Hessel et al. | 385/27 |
| 5,121,740 A | * | 6/1992 | Uram | 600/108 |
| 5,275,593 A | * | 1/1994 | Easley et al. | 606/4 |
| 5,313,070 A | * | 5/1994 | Vala et al. | 250/559.08 |
| 5,419,312 A | * | 5/1995 | Arenberg et al. | 600/108 |
| 5,509,095 A | * | 4/1996 | Baker et al. | 385/31 |
| 5,993,072 A | * | 11/1999 | de Juan et al. | 385/78 |
| 6,069,689 A | * | 5/2000 | Zeng et al. | 356/73 |
| 6,229,940 B1 | * | 5/2001 | Rice et al. | 385/33 |
| 6,485,414 B1 | * | 11/2002 | Neuberger | 600/182 |
| 6,519,485 B2 | * | 2/2003 | Wiesmann et al. | 600/328 |
| 6,892,013 B2 | * | 5/2005 | Furman et al. | 385/115 |
| 2002/0075460 A1 | * | 6/2002 | Kappel et al. | 353/102 |

* cited by examiner

Primary Examiner—Henry M Johnson, III
(74) Attorney, Agent, or Firm—Kevin L. Klug

(57) ABSTRACT

A coaxial illuminated laser endoscopic probe and active numerical aperture control apparatus and method of use, succinctly known as an illumination and laser source, capable of selectively providing illumination light and laser treatment light through a single optical fiber. The apparatus and method is especially useful during ophthalmic surgery. The present art is capable of providing the aforesaid through an optical fiber of such small size that heretofore said fiber was only useable for laser treatment light only. The present art also, with its unique optical system, allows for two illumination light outputs from a single illumination source. The apparatus utilizes a phototoxicity risk card to calibrate the system to prior art or safe illumination levels since the unique optical system provides illumination light of greater intensity than the prior art.

26 Claims, 21 Drawing Sheets

| DESCRIPTION | INCHES (MILLIMETERS) | |
|---|---|---|
| | RADIUS 1 | RADIUS 2 |
| RADIUS OF CURVATURE | 1.7824 | 1.7824 |
| FRINGE TOL. | .5 | .5 |
| IRREGULARITY TOL. | 1/8 | 1/8 |
| FINISH | 40/20 | 40/20 |
| CLEAR APERATURE | 1.352 | 1.340 |
| FACE WIDTH OF BEVEL | | |
| C.T. | .350 | |
| C.T. TOL. | ±.001 | |
| WEDGE TIR. | ±.0005 | |
| DIAMETER | 1.450 | |
| DIAMETER TOL. | +.000 −.002 | |
| MATERIAL | | |
| TYPE | S−BSM−81 | |
| GRADE | | |
| ANNEAL | | |
| MELT | | |
| COATING | | |
| R1 | R2 | |
| AR VIS. | N/A | |

| DESCRIPTION | INCHES (MILLIMETERS) | |
|---|---|---|
| | RADIUS 1 | RADIUS 2 |
| RADIUS OF CURVATURE | −1.7824 | −12.554 |
| FRINGE TOL. | .5 | .5 |
| IRREGULARITY TOL. | 1/8 | 1/8 |
| FINISH | 40/20 | 40/20 |
| CLEAR APERATURE | 1.340 | 1.340 |
| FACE WIDTH OF BEVEL | | |
| C.T. | .100 | |
| C.T. TOL. | ±.001 | |
| WEDGE TIR. | ±.0005 | |
| DIAMETER | 1.450 | |
| DIAMETER TOL. | +.000 −.002 | |
| MATERIAL | | |
| TYPE | SF−11 | |
| GRADE | | |
| ANNEAL | | |
| MELT | | |
| COATING | | |
| R1 | R2 | |
| N/A | AR VIS. | |

| DESCRIPTION | INCHES (MILLIMETERS) | |
|---|---|---|
| | RADIUS 1 | RADIUS 2 |
| RADIUS OF CURVATURE | 1.6807 | −5.8471 |
| FRINGE TOL. | .5 | .5 |
| IRREGULARITY TOL. | 1/8 | 1/8 |
| FINISH | 40/20 | 40/20 |
| CLEAR APERATURE | 1.310 | 1.288 |
| FACE WIDTH OF BEVEL | | |
| C.T. | .185 | |
| C.T. TOL. | ±.001 | |
| WEDGE TIR. | ±.0005 | |
| DIAMETER | 1.450 | |
| DIAMETER TOL. | +.000 / −.002 | |
| MATERIAL | | |
| TYPE | S−BSM−81 | |
| GRADE | | |
| ANNEAL | | |
| MELT | | |
| COATING | | |
| R1 | R2 | |
| AR VIS. | AR VIS. | |

| DESCRIPTION | INCHES (MILLIMETERS) | |
|---|---|---|
| | RADIUS 1 | RADIUS 2 |
| RADIUS OF CURVATURE | .6601 | -.8302 |
| FRINGE TOL. | .5 | .5 |
| IRREGULARITY TOL. | 1/8 | 1/8 |
| FINISH | 40/20 | 40/20 |
| CLEAR APERATURE | .900 | .800 |
| FACE WIDTH OF BEVEL | | |
| C.T. | .250 | |
| C.T. TOL. | ±.001 | |
| WEDGE TIR. | ±.0005 | |
| DIAMETER | 1.000 | |
| DIAMETER TOL. | +.000 / -.002 | |
| MATERIAL | | |
| TYPE | S-BSM-81 | |
| GRADE | | |
| ANNEAL | | |
| MELT | | |
| COATING | | |
| R1 | R2 | |
| AR VIS. | AR VIS. | |

COAXIAL ILLUMINATED LASER ENDOSCOPIC PROBE AND ACTIVE NUMERICAL APERTURE CONTROL

This application claims priority of U.S. Provisional Patent Applications No. 60/490,399 filed Jul. 28$^{th}$, 2003, and No. 60/550,979 filed Mar. 5$^{th}$, 2004, both entitled Coaxial Illuminated Laser Endoscopic Probe and Active Numerical Aperture Control and No. 60/577,740 entitled Medical Light Intensity Phototoxicity Control Card filed Jun. 5$^{th}$, 2004, and No. 60/577,618 entitled Photon Illumination and Laser Ferrule filed Jun. 5$^{th}$, 2004.

BACKGROUND OF THE INVENTION

The art of the present invention relates to fiberoptic endoscopic probes for vitreoretinal surgery in general and more particularly to an apparatus and method for delivery of both broad spectrum illumination and coherent laser treatment pulses through a common optical fiber. The present invention also provides surgical illumination intensity control by providing an apparatus and method for quickly and easily providing a fiber optic illumination light output intensity reference to ophthalmic surgeons. The present invention also utilizes a unique fiber optic connector ferrule which uniquely indicates to the aforesaid apparatus source whether the fiber is designed, best suited, or desired for illumination or laser transmission light or both. Also integral to the present invention is an optical power meter, preferably for measurement of laser output power emanating from the optical fiber.

Prior art vitreoretinal surgical procedure utilizes discrete and separate optical fibers for the delivery of typically non-coherent light for illumination and coherent laser beam light for surgical treatment of tissues. Although prior art "illuminated laser probes" of various configurations have been developed, they all utilize separate optical fiber or fibers for the non-coherent illumination stream and the coherent laser delivery. The aforesaid fibers are typically arranged side by side inside of a common needle lumen. An embodiment of this prior art technology is found in U.S. Pat. No. 5,323,766, issued to Uram. This prior art technology requires a larger or more than one incision in order to introduce illumination and laser treatment light into the eye or other structure, thereby generating greater trauma to the surgical site.

Prior art devices typically utilize a laser deliver core optical fiber diameter of typically 200 to 300 microns since said diameter provides the surgical laser burn spot size most commonly desired by the surgeon. The aforesaid prior art devices have been unable to provide sufficient surgically useful illumination (non-coherent white light) power through such a small fiber, primarily due to the prior art's inability to focus said non-coherent surgically useful light onto such a small spot size. Moreover, none of the prior art devices have combined the aforesaid surgically useful illumination and laser treatment light and transmitted through a single fiber, especially of the aforesaid small size.

The present art apparatus and method provides coaxial delivery of both broad spectrum illumination and coherent laser treatment pulses through a common optical fiber. In a preferred embodiment, the apparatus first comprises a non-coherent light source (coherent in an alternative embodiment) capable of coupling sufficient illumination light into an optical fiber with a core diameter suitable for vitreoretinal laser treatment light delivery. That is, to provide a volume of light to the surgical site which is sufficient for illumination of the surgical procedure. In a preferred embodiment said core fiber diameter is typically 200 to 300 microns since said diameter provides the surgical laser burn spot size most commonly desired by the surgeon. The aforesaid optical fiber is typically a multi-mode stepped index fiber in a preferred embodiment. Alternative embodiments may vary the type and size of the optical fiber without departing from the scope of the present art.

An object of the present invention is to utilize a light source capable of using 250 micron (or smaller) optical fibers while still providing similar surgically useful lumen output to current 750 micron fiber sources (typically 10–12 lumens). The source output aperture of the present invention in a preferred embodiment is at least 0.5 na (numerical aperture). Alternative embodiments may vary this numerical aperture without departing from the scope of the present invention. The color of the light delivered by the present invention appears white despite the light power output or intensity. Also, the output intensity is capable of reduction without significantly affecting the color, aperture, or homogeneity of the light. The output bandwidth of the aforesaid light is substantially limited to the visible spectrum, that is both UV and IR light are minimized. An option for user selectable Limitations (separate from the UV and IR limitations) in the output spectrum is provided. Apparatus conformance to relevant safety standards is also provided.

Prior art illumination light sources typically require a minimum aggregate optical fiber core area equivalent to a fiber diameter of approximately 500 microns in order to deliver sufficient illuminating light to be considered useful by the surgeon. A fundamental prior art limitation with utilization of smaller light fibers for illumination is the size of the focus spot in the light source itself. In a preferred embodiment, the art of the present invention utilizes a small geometry arc lamp which is capable of focusing to an extremely small illumination spot size due to its extremely small plasma ball. This focusing attribute allows for efficient coupling of illumination light into an optical fiber of 100 to 300 micron core diameter which is typically utilized for laser treatment light delivery. Utilization of the aforesaid preferred embodiment allows for up to 40 milliwatts of illumination light to be delivered by a fiber previously considered too small to be an efficient illumination light source.

The aforesaid present art light source includes an input aperture or connector for the attachment of a laser coupling fiber. The aforesaid aperture attachment is somewhat similar to the method by which a treatment laser is attached with an ophthalmic slit lamp. That is, via a fiber optic pigtail typically equipped with a mechanical output connector such as an exi sma. In the preferred embodiment, dichroic optics and/or other optical path design techniques are used to coaxially couple a treatment laser beam into the illumination optical path, and into an endoscopic probe optical fiber. That is, with the aforesaid coupling arrangement (using a single fiber), the present art apparatus and method allows a unique single and smaller optical fiber to be utilized for both illumination and laser treatment purposes. The art of the present invention further provides a new generation of vitreo-retinal endoscopic instrumentation which utilizes the prior art space occupied by larger illumination fibers and is also capable of providing such in a smaller cross-sectional fiber bundle.

The present art accepts laser light from various surgical laser sources, mixes said laser light with illumination light, and launches both down a single fiber. Laser output aperture is minimized and the laser light is not substantially affected by the illumination dimming or other spectral output limiting. An aiming beam is visible within the illumination output pattern. Unique to the present part is a shadow appearance in the output light cone which indicates the location of laser treatment upon activation of a laser light source. Power losses through the system are also minimized. As aforesaid, the laser mixing method does not significantly affect illumination when not in use (i.e. color, aperture, or homogeneity).

Another unique feature of the present art invention is the ability to change the angular light output from an endoscopic probe coupled with the aforesaid coaxial optical fiber by actively controlling the focus characteristics of the light source. That is, prior art light sources have a fixed numerical aperture focus configuration which is typically designed to fill the full acceptance cone of the mating optical illumination fiber. The present art invention further comprises and utilizes surgeon controlled condensing optics to provide a variable focused light output from the endoscopic probe and efficient coupling into different fiber types. This is especially useful for coupling with optical fibers having different numerical aperture requirements.

Ophthalmic surgical illumination devices for use with optical fibers are found in the prior art and have been manufactured by numerous companies for years. One of many such devices is described in U.S. Pat. No. 4,757,426 issued to Scheller, et al. on Jul. 12, 1988, Entitled "*Illumination System for Fiber Optic Lighting Instruments*". One of the most widely used illumination devices is the "Millennium" which is manufactured by Bausch and Lomb®. Other manufacturers are Alcon® with the "Accurus" and Grieshaber® with the "GLS150". Due to the prevalence of the aforesaid within the marketplace, it is desirable for new and high intensity illumination devices, such as the present art device, to provide an intensity reference indication to ophthalmic surgeons which allows them to reliably duplicate or mimic the illumination intensity of one or more of the aforesaid prior art devices. This is especially true since retinal photic injury is a possible complication of the need to use bright light to clearly visualize ocular structures during delicate ophthalmic surgical procedures. The present art invention further represents a novel apparatus and method for providing the ophthalmic surgeon with graphical phototoxicity risk information in a clear and easy to understand manner. In a preferred embodiment, it is comprised of an inexpensive card that is removably attached to the control panel of a surgical light source in order to show the relationship between the output intensity of the light source and the likelihood of photic injury.

Further included with the present art apparatus is an integral optical power meter which is in a preferred embodiment, capable of measuring the laser power output emanating from the fiber optic. Alternative embodiments of said laser power meter also measure the illumination power intensity.

Accordingly, it is an object of the present invention to provide a coaxial illuminated laser endoscopic probe and active numerical aperture control apparatus and method of use which is capable of transmitting both illumination (non-coherent) and laser (coherent) treatment light through a single optical fiber of sufficiently small diameter that said fiber may be used for laser treatment, especially in eye surgical or ophthalmic applications.

Another object of the present invention is to provide a coaxial illuminated laser endoscopic probe and active numerical aperture control apparatus and method of use which provides both a surgically useful illumination (non-coherent) output and a combined laser (coherent) output.

Another object of the present invention is to provide a coaxial illuminated laser endoscopic probe and active numerical aperture control apparatus and method of use with an illumination intensity control which is usable by the surgeon to control illumination intensity without affecting laser output power or laser beam spot size characteristics or illumination spectral content.

A further object of the present invention is to provide a coaxial illuminated laser endoscopic probe and active numerical aperture control apparatus and method of use which connects with conventional laser light sources.

A further object of the present invention is to provide a coaxial illuminated laser endoscopic probe and active numerical aperture control apparatus and method of use which provides a shadow or aiming hole within the illumination light cone projection where the laser treatment is placed.

A still further object of the present invention is to provide a coaxial illuminated laser endoscopic probe and active numerical aperture control apparatus and method of use which provides an intensity reference indication to ophthalmic surgeons which allows them to reliably duplicate or mimic the illumination intensity of one or more prior art devices or allows them to understand and minimize phototoxicity risks relating to the illumination output.

A still further object of the present invention is to provide a coaxial illuminated laser endoscopic probe and active numerical aperture control apparatus and method of use which provides a unique ferrule or connector for optical fiber connection which uniquely indicates to the aforesaid apparatus source whether the optical fiber is designed, best suited, or desired for illumination or laser transmission light or both.

A yet further object of the present invention is to provide a coaxial illuminated laser endoscopic probe and active numerical aperture control apparatus and method of use which minimizes trauma to the patient and surgical site.

A yet further object of the present invention is to provide a coaxial illuminated laser endoscopic probe and active numerical aperture control apparatus and method of use which has an integral power meter for measurement of laser output power.

SUMMARY OF THE INVENTION

To accomplish the foregoing and other objects of this invention there is provided a device for providing non-coherent illumination light and coherent laser treatment light through a single optical fiber of the size typically used for laser treatment only. The apparatus is especially suited for use during ophthalmic surgery.

The present art, in a preferred embodiment, utilizes a 75 watt xenon arc lamp for its high luminance illumination (light density), greater than 6000° K color temperature, and greater than 95 color rendering index. The xenon arc lamp further provides an extremely small point light source which allows for a smaller output illumination beam diameter. Unique to the present lamp source is a mount which allows for replacement of the lamp and yet retains the location of the plasma ball of said source precisely at a predetermined location within the optical center of the apparatus.

A classic spherical reflector and two lens light collection layout is utilized rather than other lower part count layouts, such as using an elliptical reflector or a combination of a parabolic reflector and lens. Light that is incident on the reflector is reflected back to the lamp. A first achromatic lens collimates light from the source and the upside down or inverted image. A second achromatic lens is located coaxial to the first lens and focuses the light at its focal point. The optical fiber is located at the focal point of the second lens. The aforesaid reflectors are preferably spherical rather than parabolic in order to reflect illumination light in the same form as sourced from the arc lamp.

An additional separate illumination path is possible with the present art. No other conventional illumination light source incorporates multiple light paths from a single lamp. The independent nature of the two paths allow different filtering and intensity control settings to the two outputs.

Output dimming of the present art illumination is accomplished by steering the first (collimating) or penultimate lens in a fashion that does not change the lens numerical aperture or introduce shadow artifacts into the beam. A control knob allows the user to select the desired illumination level by rotating the knob.

The output optical fiber connector is uniquely configured to provide the precise positioning required while reducing cost. A precise connector end is combined with an integral retention thread to reduce parts cost and assembly time. An optional groove or recess is placed on a second version of the connector to provide for sensing the difference between illumination only and laser compatible output fibers. Placement of a smooth diameter connector into the output activates a switch which will allow the laser power to be mixed. Either the lack of a connector or the groove under the switch will cause the switch to not activate and the laser power will not be mixed in.

Regarding mixing of laser treatment energy or light, laser light is delivered to the system via a preferably 50 micron optical fiber or equivalent. Laser light exiting the delivery fiber is preferably collimated using a 16 mm focal length achromatic lens or equivalent. If all safety requirements are met (i.e. laser output compatible fiber inserted and selection switch for laser output activated) a steering mirror reflects the collimated laser light into the center of the illumination axis. This results in the output of the fiber having a cone of white light with a shadow in the center nearly filled with the laser aiming beam (treatment beam during treatment). That is, the laser provides an aiming beam, typically red, when not fully activated for treatment and a treatment beam, typically green, when fully activated. Without the shadow caused by the steering mirror the aiming beam would be entirely washed out or imperceptible except at very low illumination levels.

As described, unique to the present art is a coaxial laser and illumination apparatus which heretofore has not been available or utilized. Also unique to the present art is a highly efficient illumination system which utilizes spherical reflectors and associated lenses to capture a maximum light output and also provide a twin path illumination light output from a single lamp source in order to feed fibers of diameter less than 500 microns which are conventionally used for laser treatment only. Further unique to the present art is a laser steering mirror having a solenoid selectability which provides an aiming hole within the illumination path for laser placement. Still further unique to the present art is an illumination arc lamp system having an extremely small point light source which allows for an extremely small illumination focus size or numerical aperture output. Also unique to the present art is an arc lamp mount which precisely places the plasma ball of the arc lamp at the focus center of the optics system. Also unique to the present art is a unique dimming mechanism which moves the focal point of a dimming lens in order to provide dimming without introducing artifacts, chromatic aberrations, or changes of color temperature. Also unique to the present art is a capability of connection with existing conventional laser light sources whereby laser treatment and illumination are both provided at an output of the present art apparatus.

The present art invention also represents a novel apparatus and method for providing the ophthalmic surgeon with graphical photoxicity risk information in a clear and easy to understand manner. In a preferred embodiment, an inexpensive card is removably attached to the control panel of the surgical light source. Preferably, the present art card is attached in close proximity to the light intensity control in order to show the relationship between the output intensity of the light source and the likelihood of photic injury. The graphical representation on the card acts as a guide for adjustment of the output intensity of the source in relationship to an accepted standard, that is such as the "Millennium" from Bausch and Lomb®. In this way the spectral and power characteristics of the various elements involved in delivering light to the eye are integrated into a single and easily manageable variable. This greatly reduces the complexity of judging the best intensity to use in a given situation.

The art of the present invention also comprises a ferrule or connector having an internal bore, preferably stepped, which is substantially parallel with the lengthwise axis of the ferrule body. The aforesaid bore allows for placement and bonding or potting of an optical fiber within and through said ferrule body. Externally, said ferrule body is also stepped in a unique form in order to optimally function as described herein.

Where provided herein, dimensions, geometrical attributes, and thread sizes are for preferred embodiment informational and enablement purposes. Alternative embodiments may utilize a plurality of variations of the aforesaid without departing from the scope and spirit of the present invention. The art of the present invention may be manufactured from a plurality of materials, including but not limited to metals, plastics, glass, ceramics, or composites.

BRIEF DESCRIPTION OF THE DRAWINGS

Numerous other objects, features, and advantages of the invention should now become apparent upon a reading of the following detailed description taken in conjunction with the accompanying drawings, in which.

DETAILED DESCRIPTION

Figure 1:
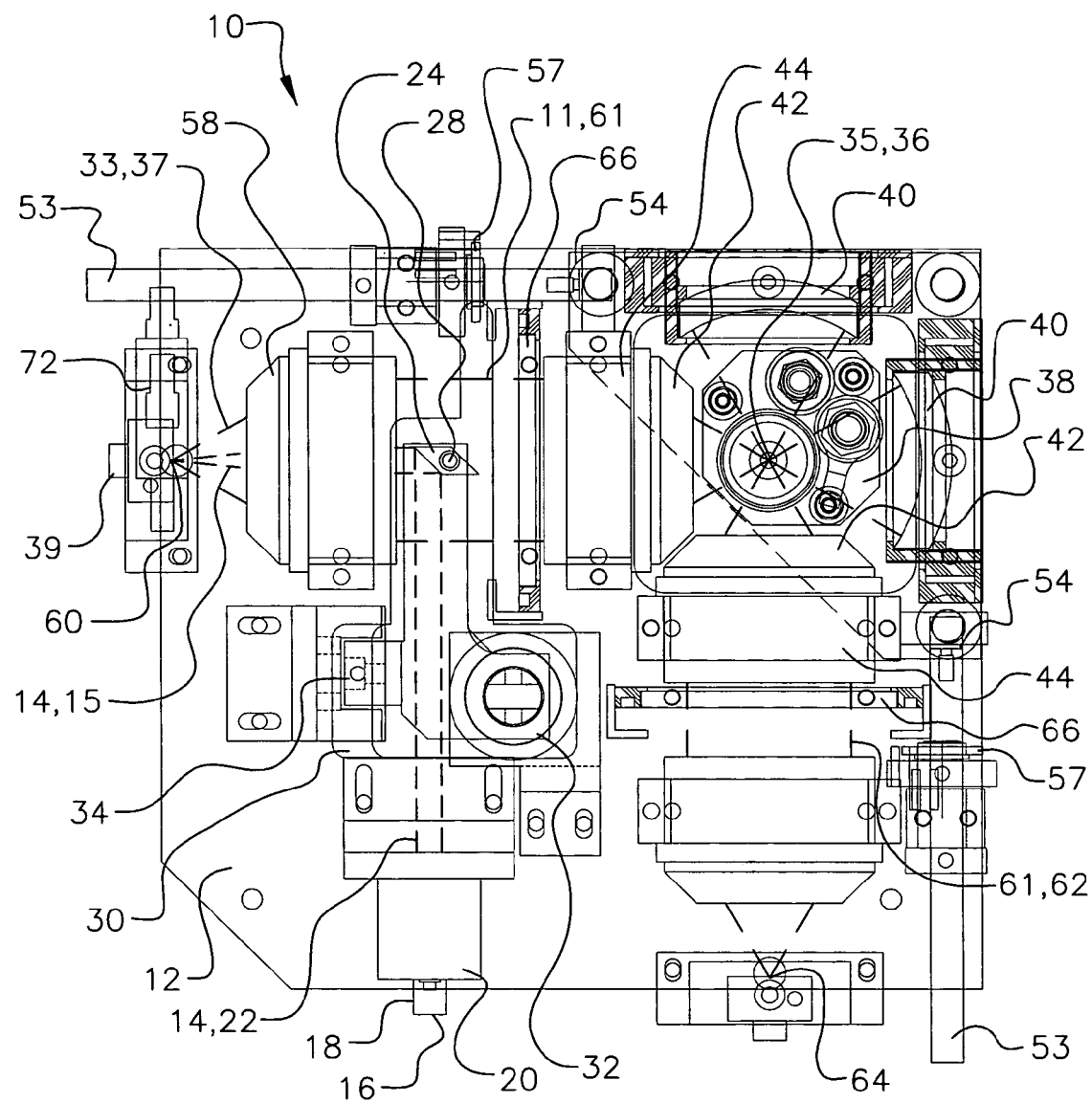
FIG. 1 is a top plan view of a preferred embodiment of the coaxial illuminated laser endoscopic probe and active numerical aperture control apparatus showing illumination and laser light paths without the phototoxicity card, power meter, and ferrule connectors.
Figure 2:
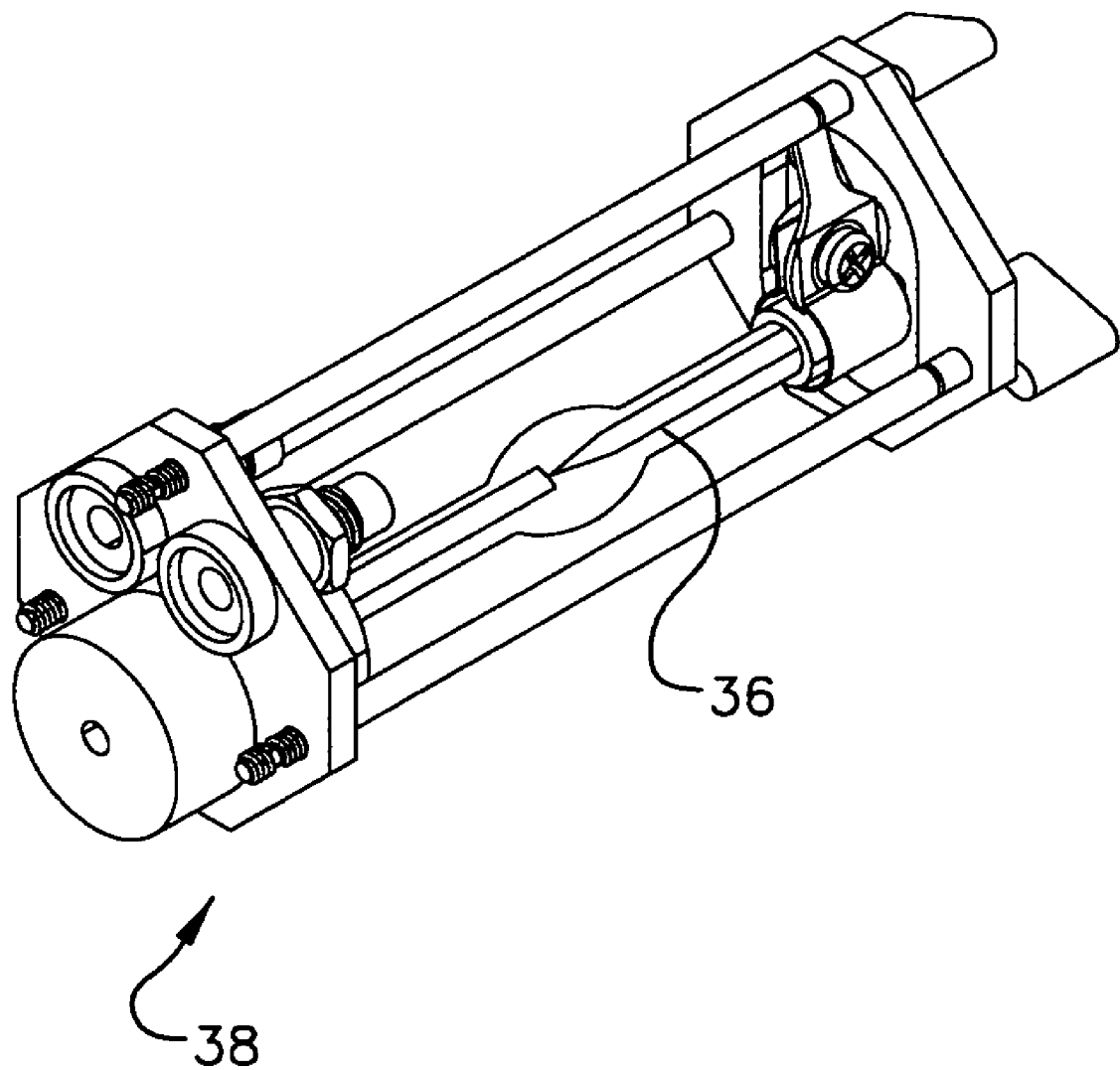
FIG. 2 is a perspective view of the arc lamp source and mount.
Figure 3:
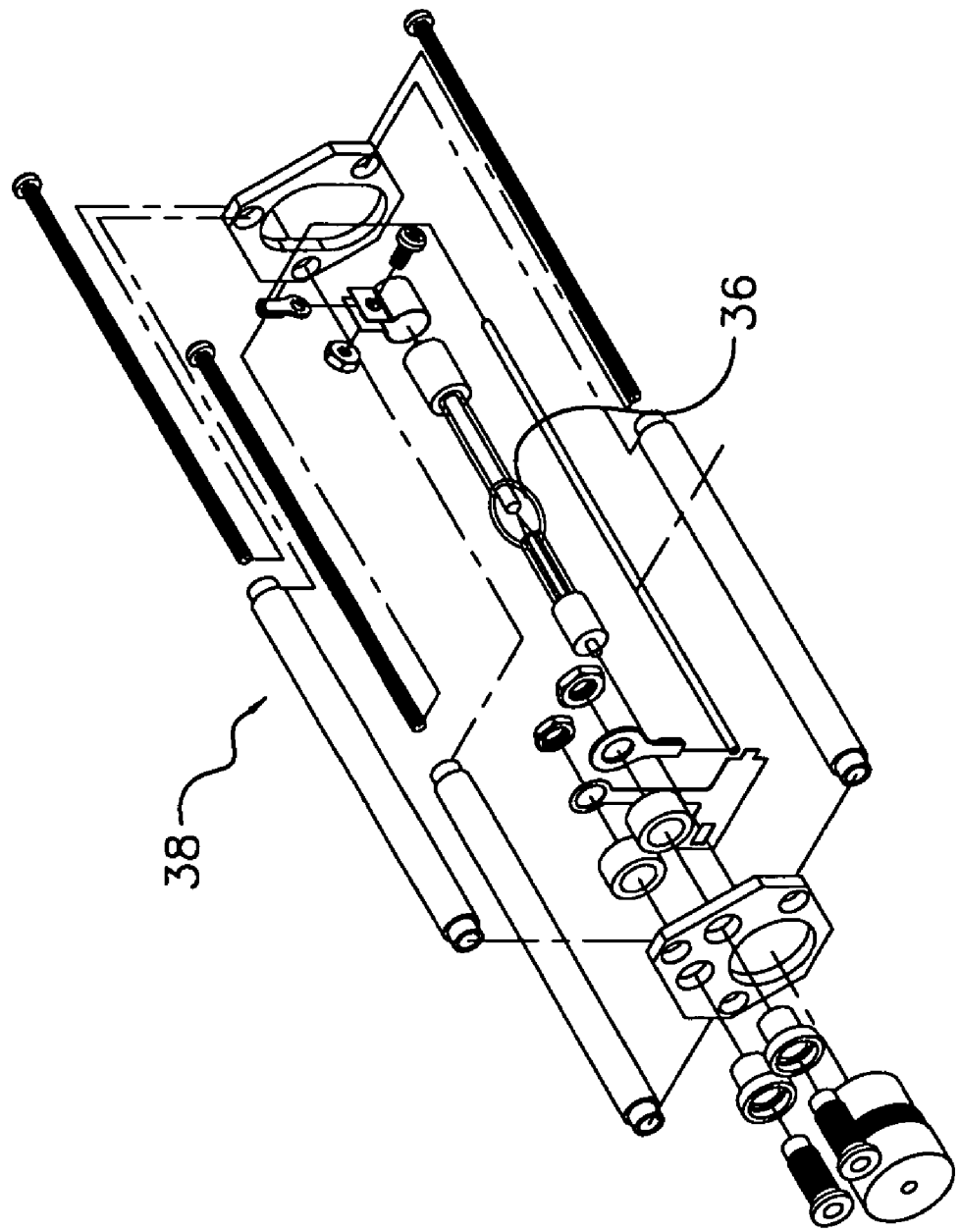
FIG. 3 is an assembly view of the arc lamp source and mount.
Figure 4:
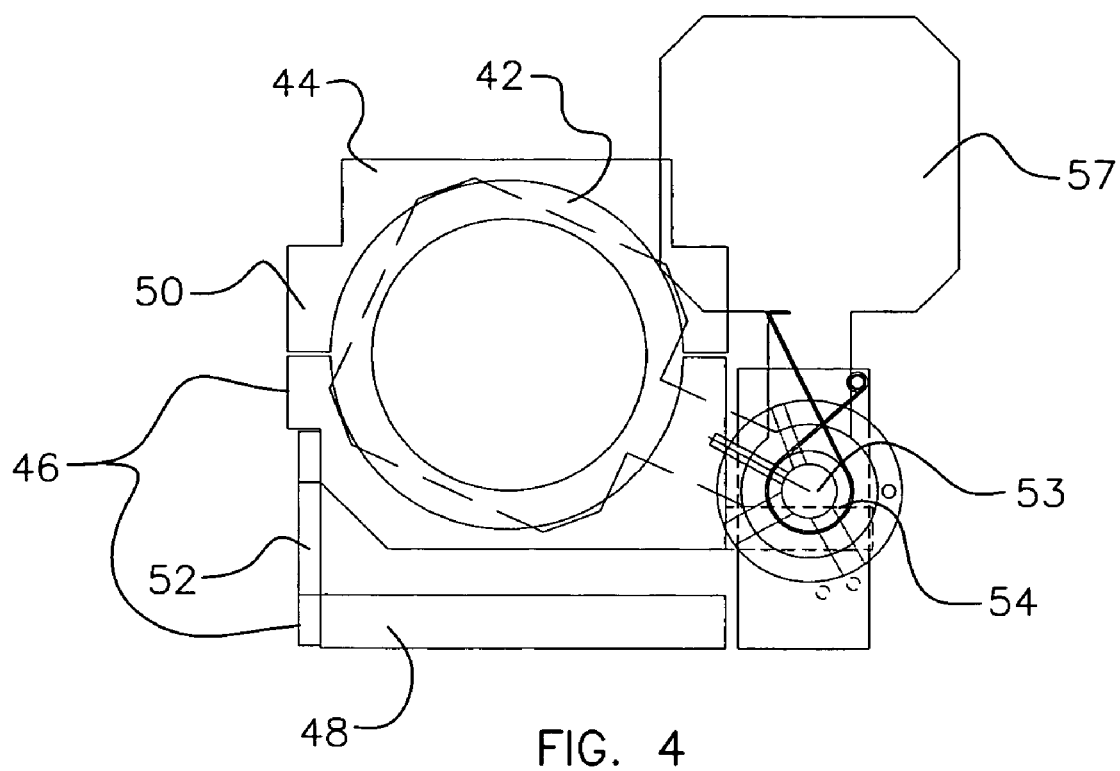
FIG. 4 is a front side plan view of the first lens mount, shaft mounted cam, and shutter with a closed position shutter shown in phantom.
Figure 5:
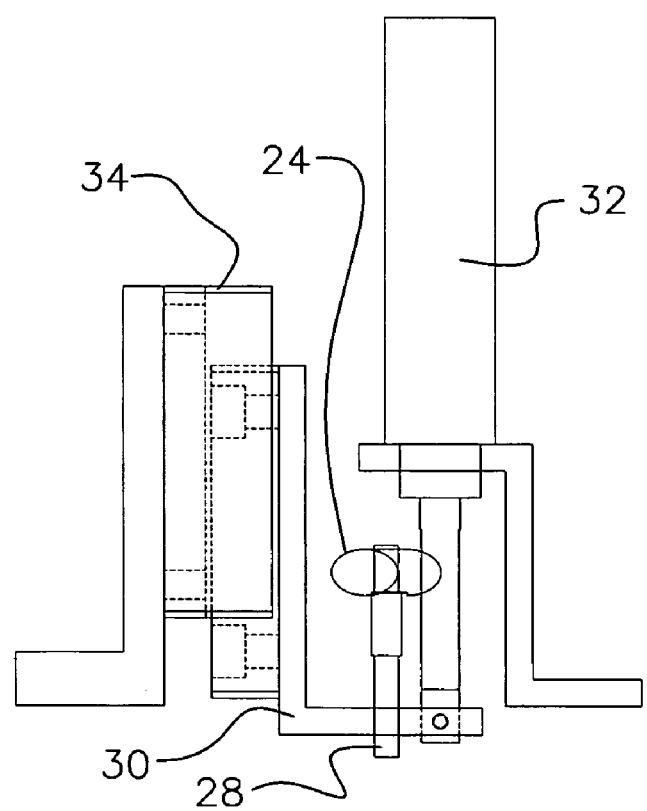
FIG. 5 is a front side plan view of the steering mirror, post, bracket, ball slide, and solenoid in a non-energized extended position.
Figure 6:
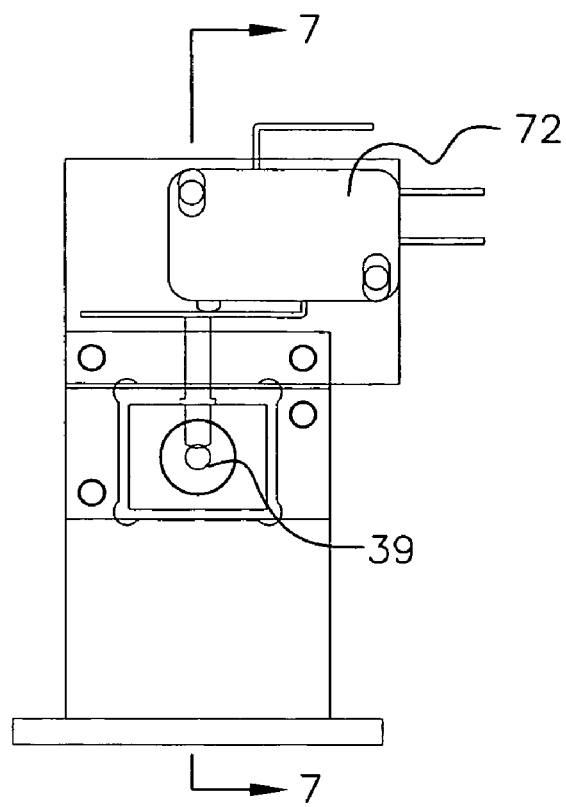
FIG. 6 front side plan view of the first output for laser and illumination light and the switch for sensing the recess in the alignment barrel.
Figure 7:
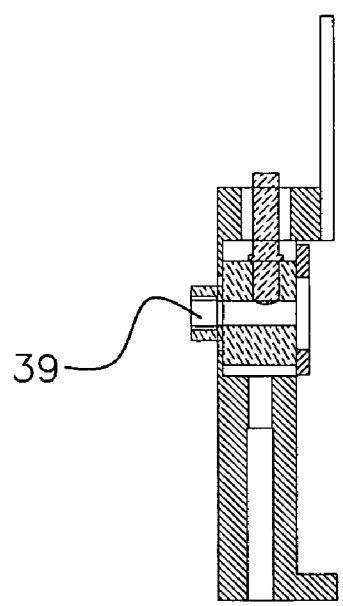
FIG. 7 is a cross sectional view taken along line 7—7 of FIG. 6 without the switch body attached.
Figure 8:
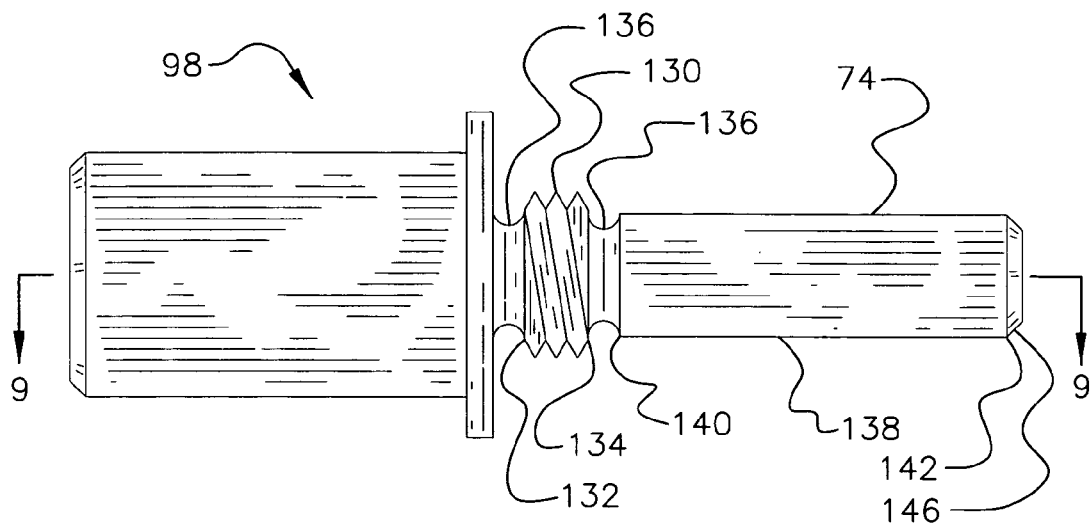
FIG. 8 is a side plan view of the ferrule connector without the recess for preferrably laser and illumination use.
Figure 9:
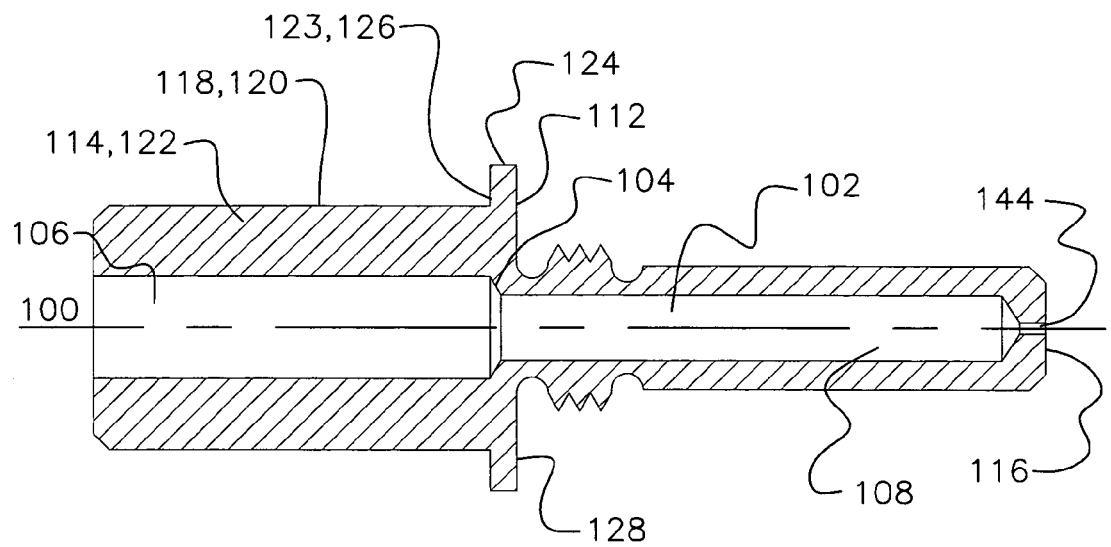
FIG. 9 is a cross sectional view taken along line 9—9 of FIG. 8.
Figure 10:
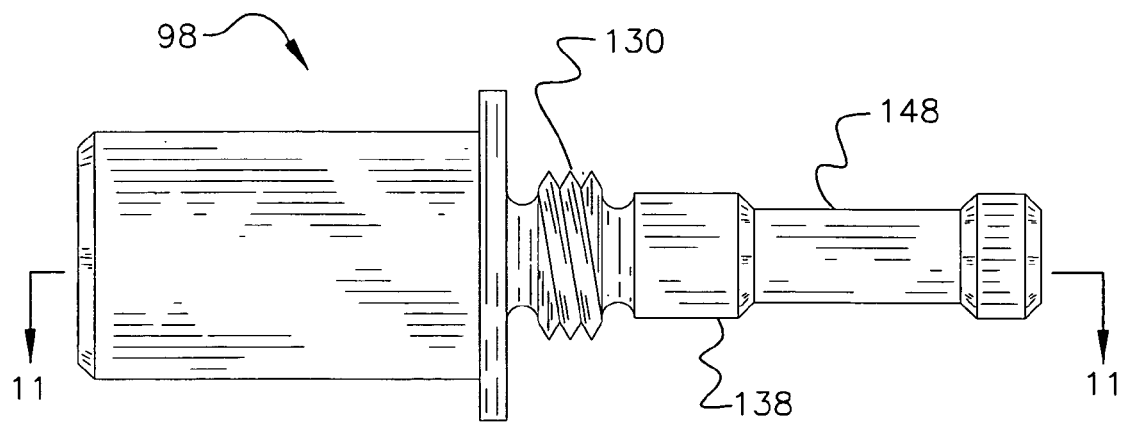
FIG. 10 is a side plan view of the ferrule connector with the recess for preferably illumination use.
Figure 11:
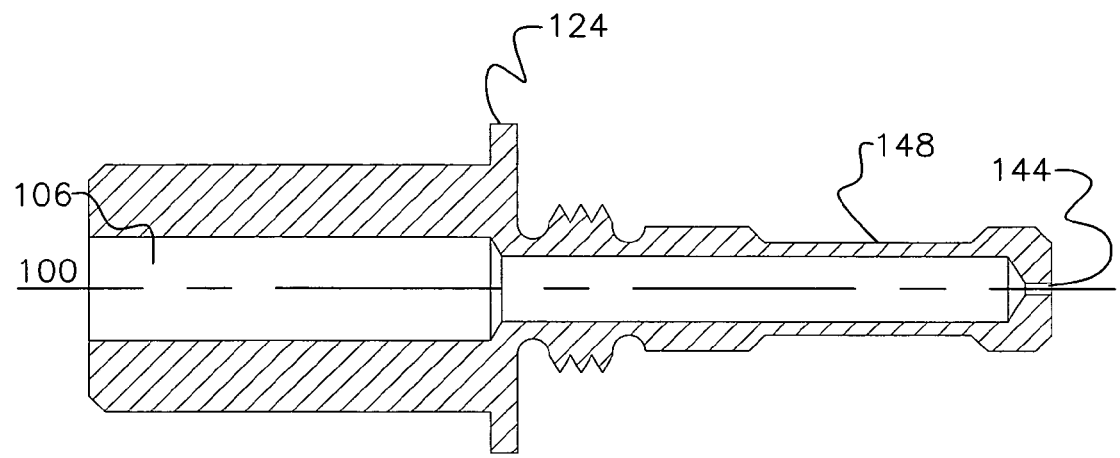
FIG. 11 is a cross sectional view taken along line 11—11 of FIG. 10.
Figure 12:
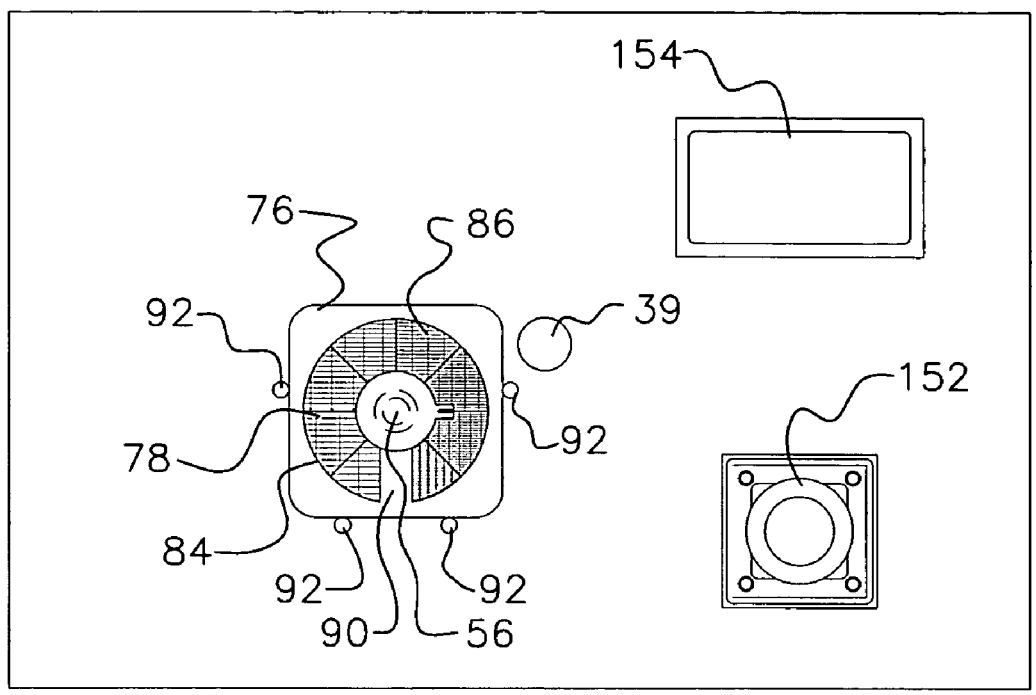
FIG. 12 is a front side plan view of the front panel of the coaxial illuminated laser endoscopic probe and active numerical aperture control apparatus housing showing the first output, illumination level control knob, photoxicity risk card, and laser power meter display and sensor.
Figure 13:
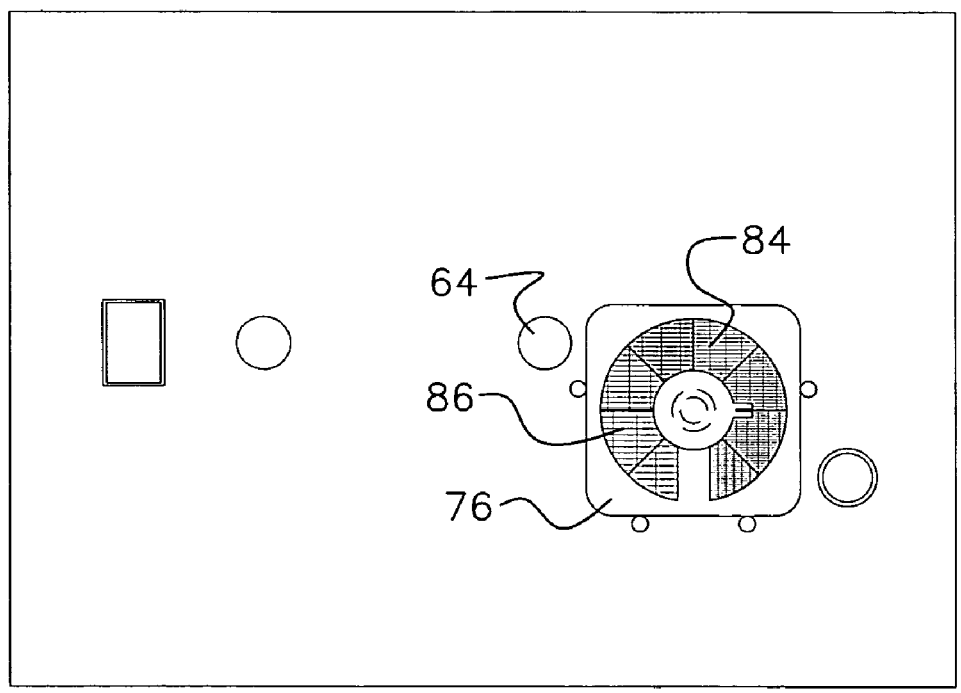
FIG. 13 is a right side plan view of the right panel of the coaxial illuminated laser endoscopic probe and active numerical aperture control apparatus housing showing the second output, illumination level control knob, laser connector, power and laser switches, and photoxicity risk card.
Figure 14:
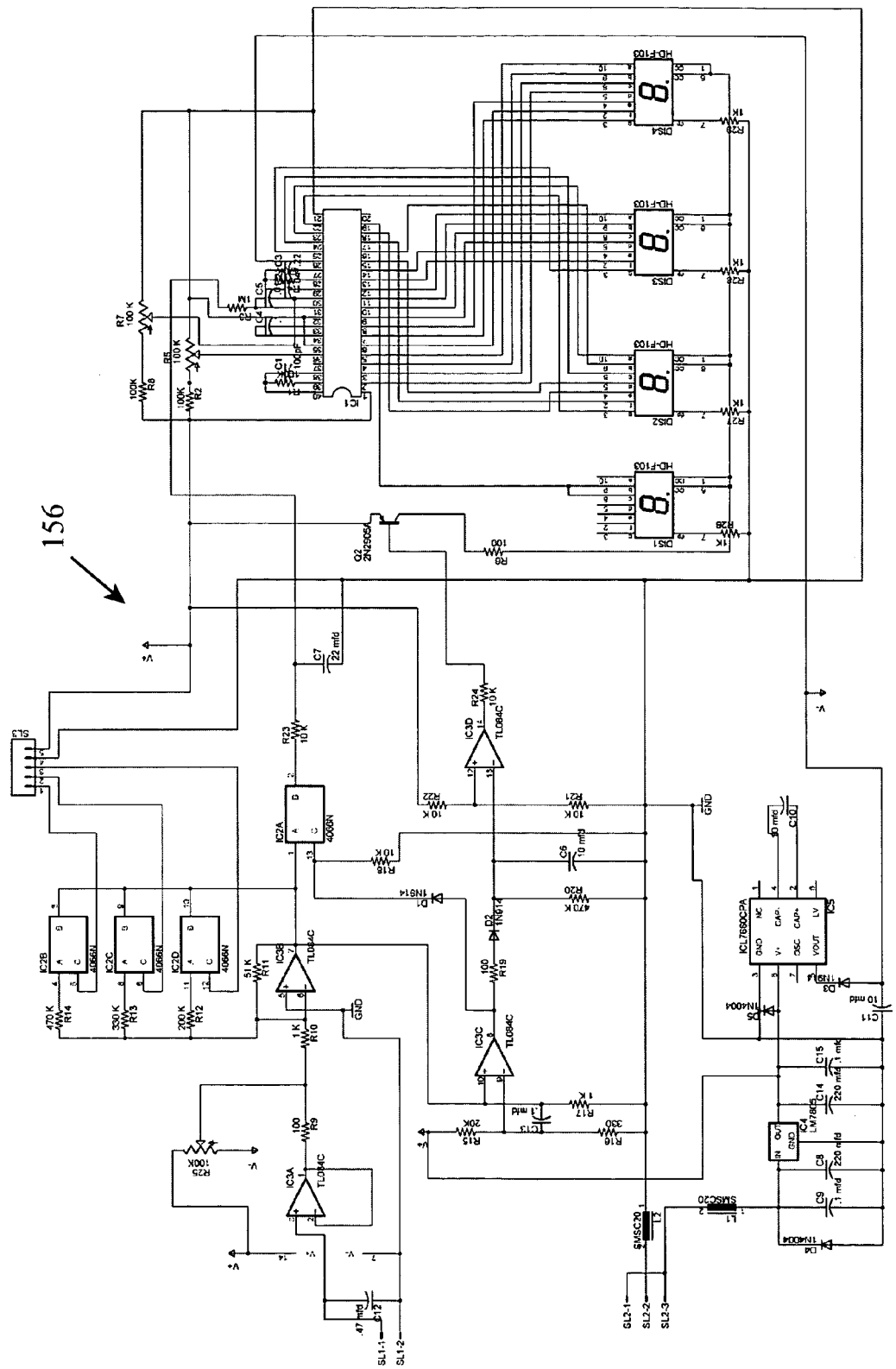
FIG. 14 is an electronic schematic diagram of the laser power meter circuitry.
Figure 15:
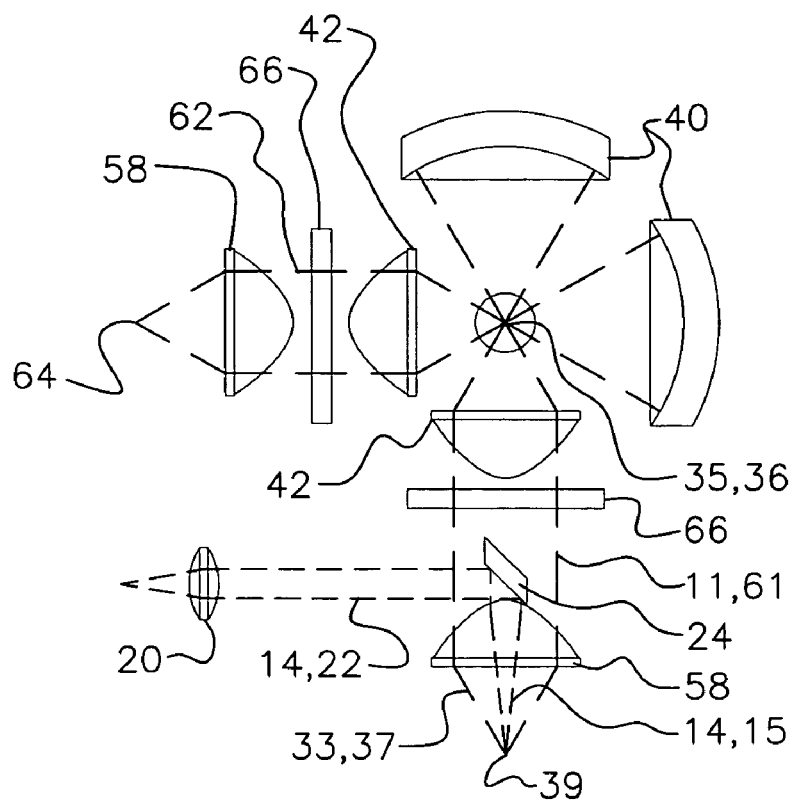
FIG. 15 is an optical schematic diagram of the preferred embodiment of the coaxial illuminated laser endoscopic probe and active numerical aperture control apparatus showing laser and illumination rays, reflectors, mirrors, and lenses.
Figure 16:
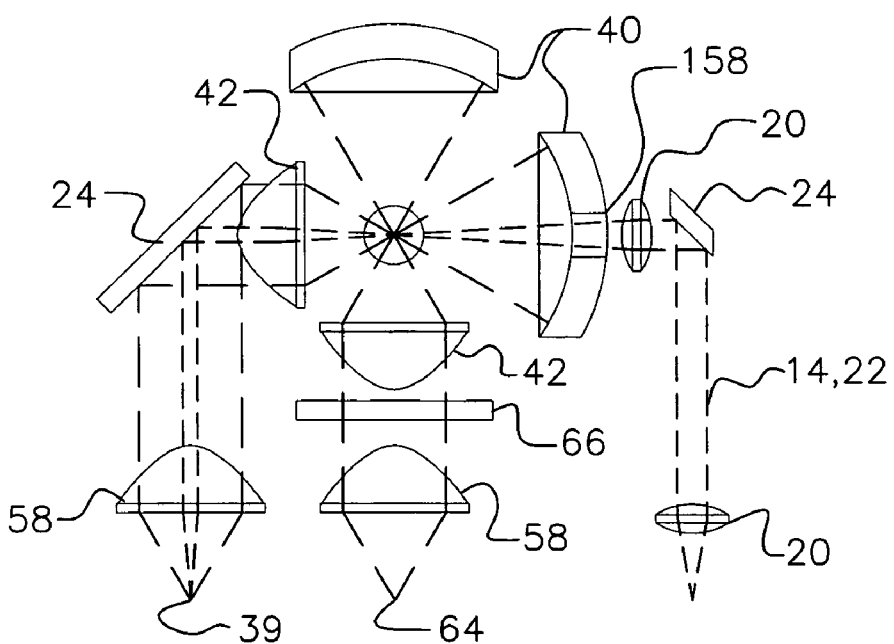
FIG. 16 is an optical schematic diagram of an alternate embodiment of the coaxial illuminated laser endoscopic probe and active numerical aperture control apparatus showing laser and illumination rays, reflectors, mirrors, and lenses.
Figure 17:
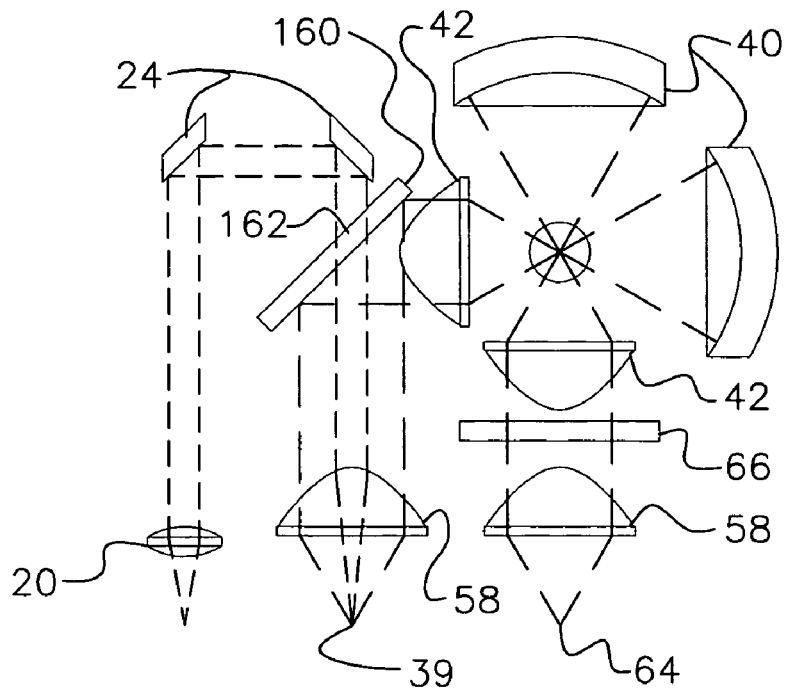
FIG. 17 is an optical schematic diagram of a further alternate embodiment of the coaxial illuminated laser endoscopic probe and active numerical aperture control apparatus showing laser and illumination rays, reflectors, mirrors, and lenses.
Figure 18:
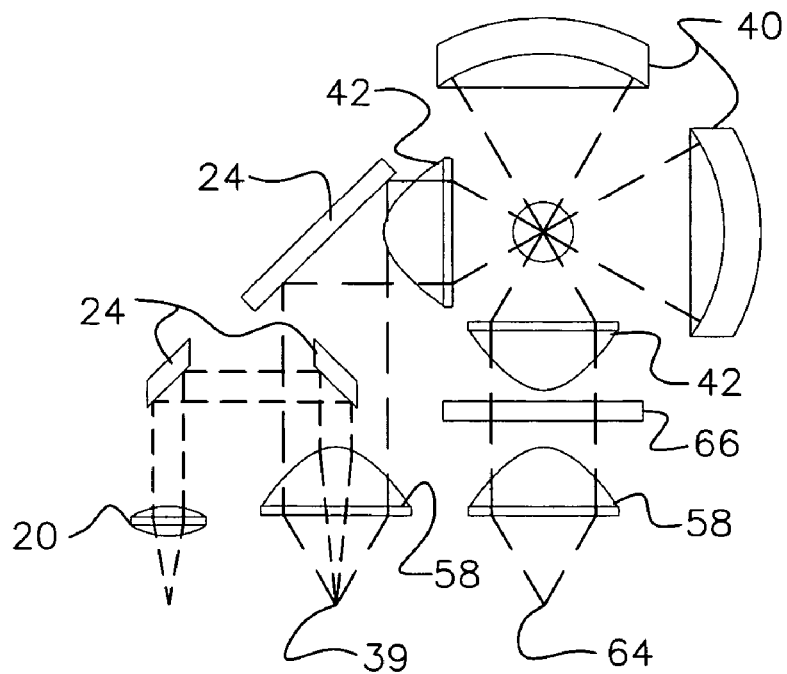
FIG. 18 is an optical schematic diagram of another alternate embodiment of the coaxial illuminated laser endoscopic probe and active numerical aperture control apparatus showing laser and illumination rays, reflectors, mirrors, and lenses.
Figures 19, 20:
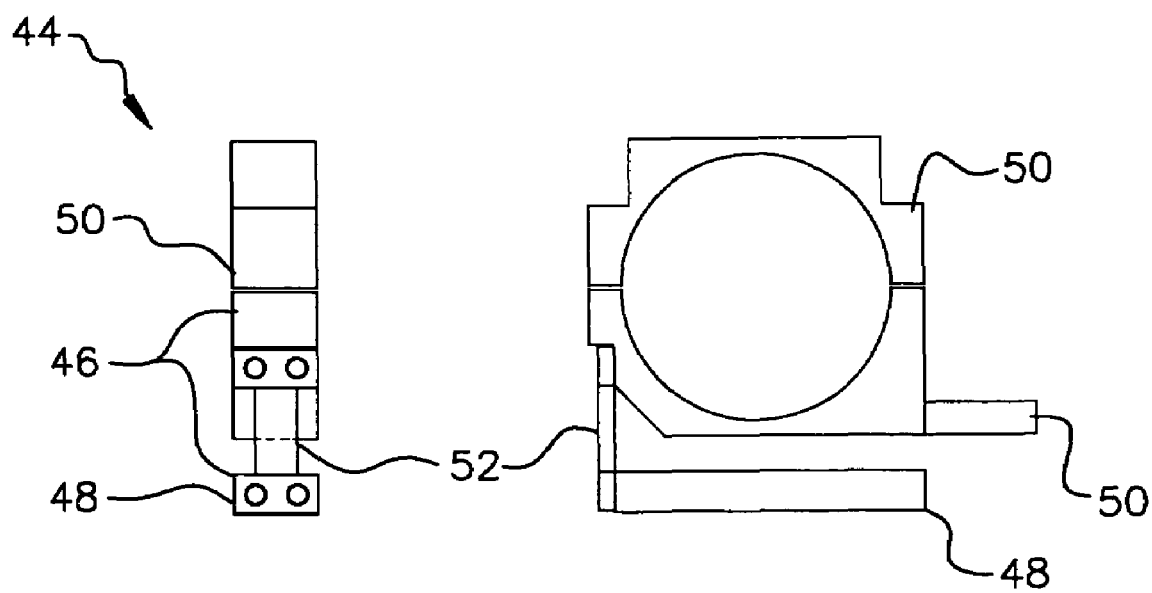
FIG. 19 shows a left side plan view of the first lens mount.
FIG. 20 shows a front side plan view of the first lens mount at a full intensity position
Figure 21:
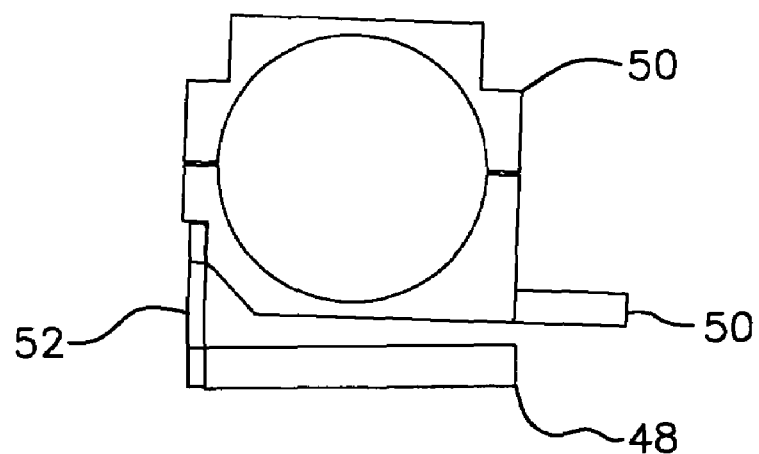
FIG. 21 shows a front side plan view of the first lens mount at a dimmed intensity position.
Figure 22:
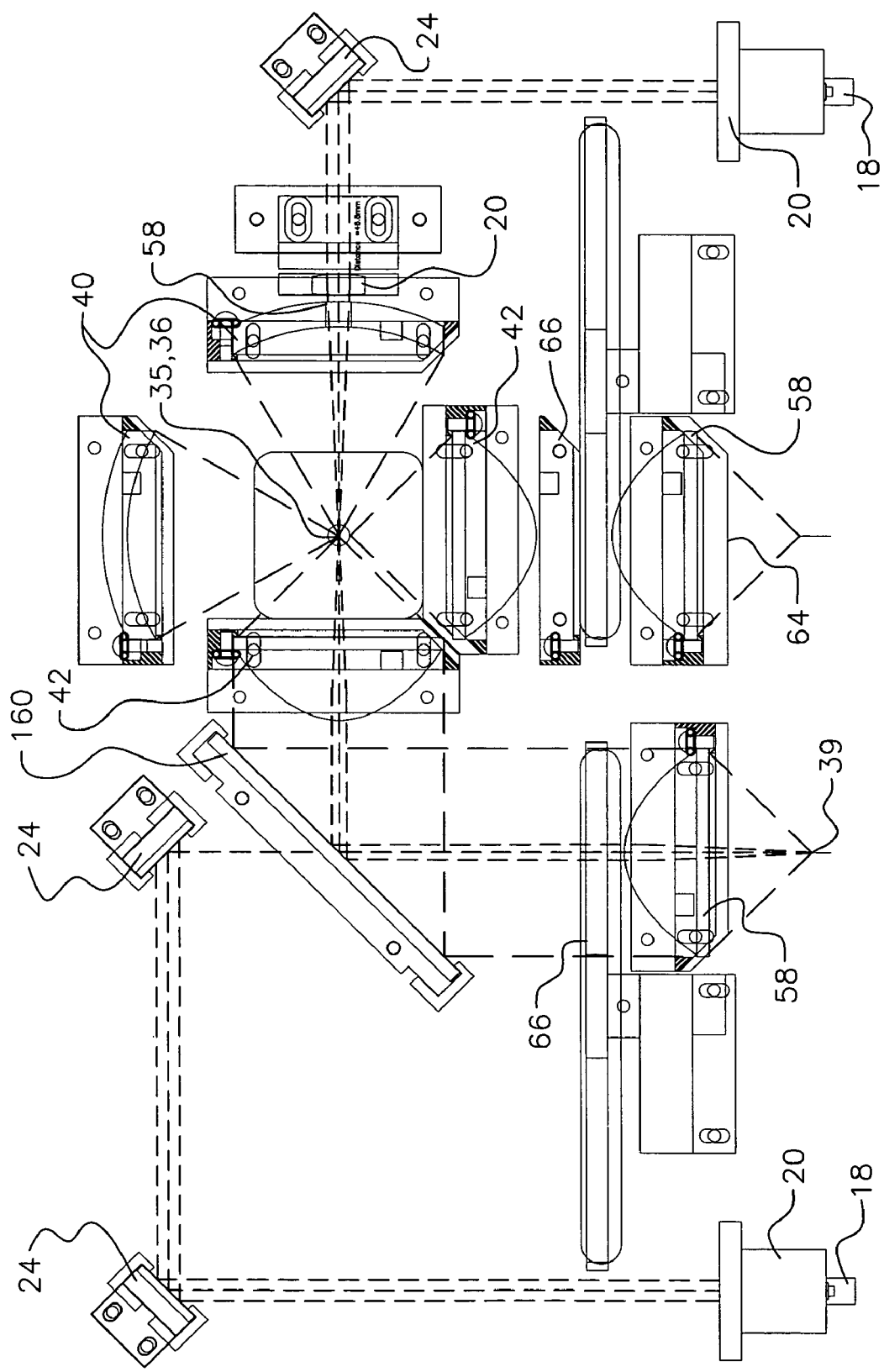
FIG. 22 shows a top plan view of an implementation of the alternate embodiments of the coaxial illuminated laser endoscopic probe and active numerical aperture control apparatus as shown in the optical schematics of FIGS. 16 & 17 showing illumination and laser light paths without the phototoxicity card, power meter, and ferrule connectors.
Figure 23:
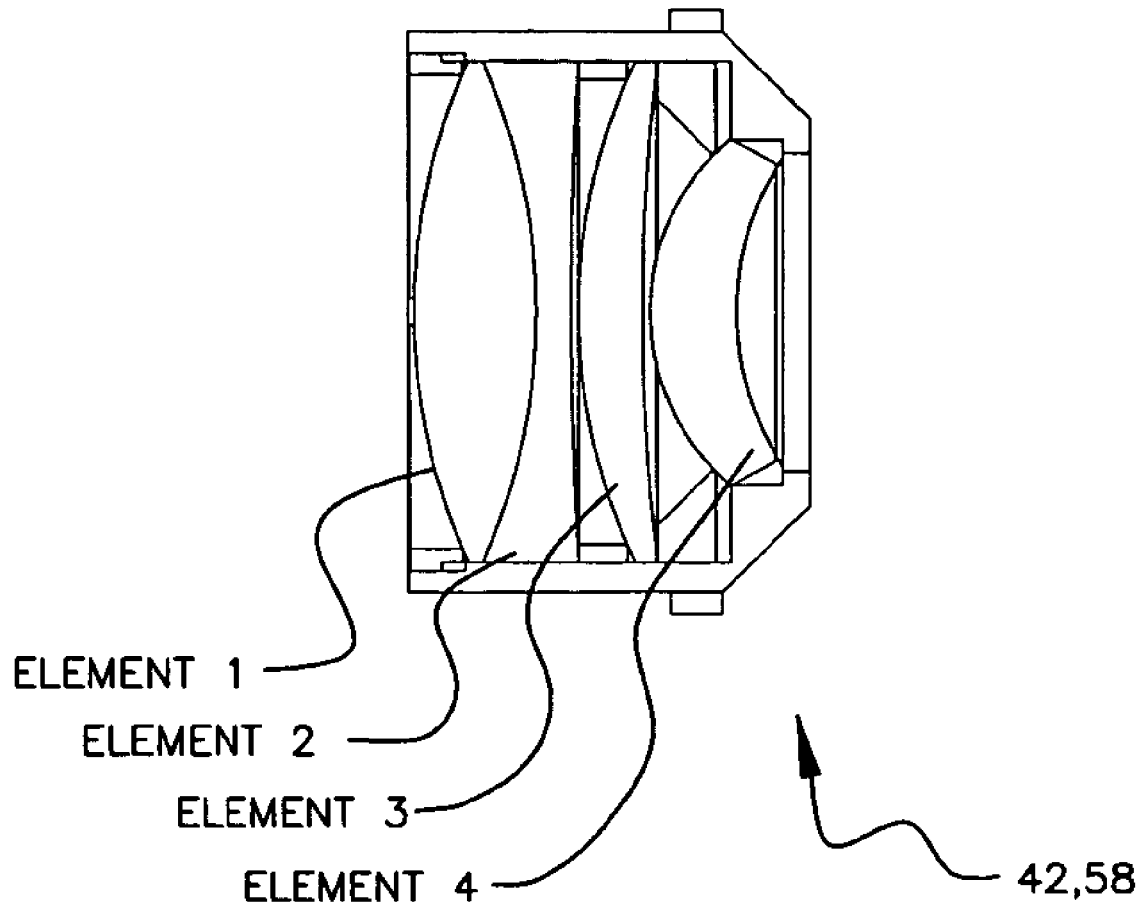
FIG. 23 shows a side plan half cross sectional view of the preferred embodiment of the first and second lenses which correct for color, spherical aberration, and coma and have a back focus 20 mm from the apex of the last element and a numerical aperture of 0.5.
Figure 24:
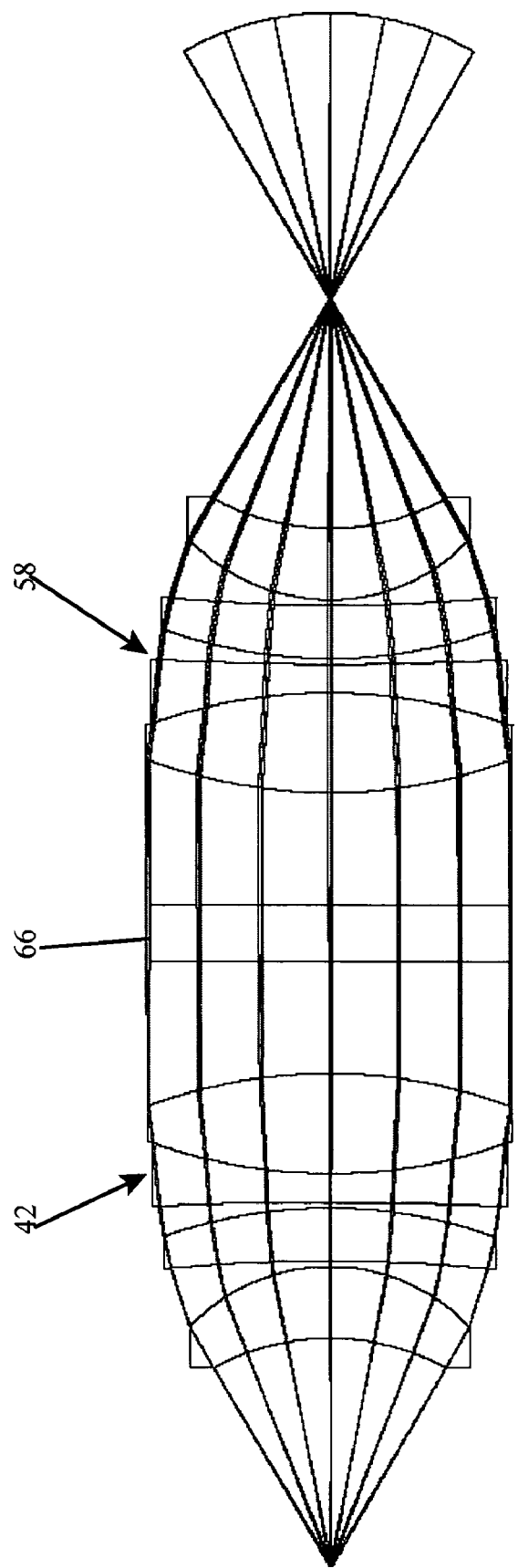
FIG. 24 shows an optical schematic of the first lens set, collimated space, dichroic hot mirror filter, and second lens set with illumination light path rays shown.
Figure 25:
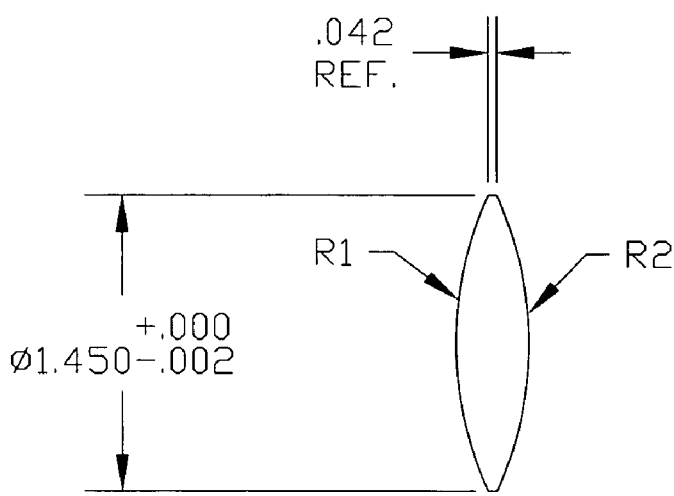
FIG. 25 shows a detailed side plan half cross sectional view with dimensional attributes of the preferred embodiment of element 1 of the lens shown in FIG. 23.
Figure 26:
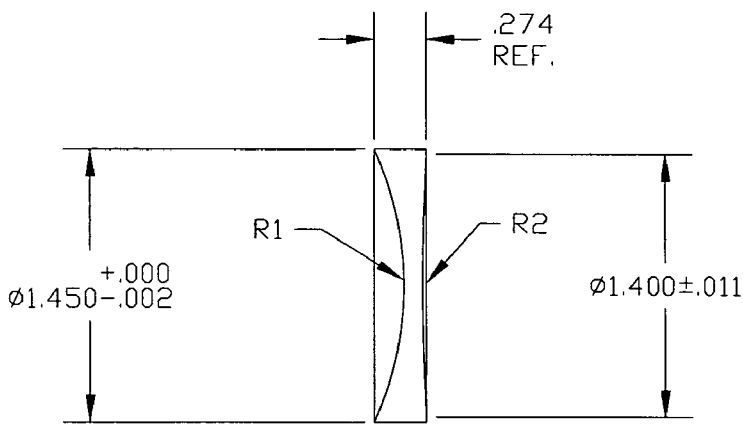
FIG. 26 shows a detailed side plan half cross sectional view with dimensional attributes of the preferred embodiment of element 2 of the lens shown in FIG. 23.
Figure 27:
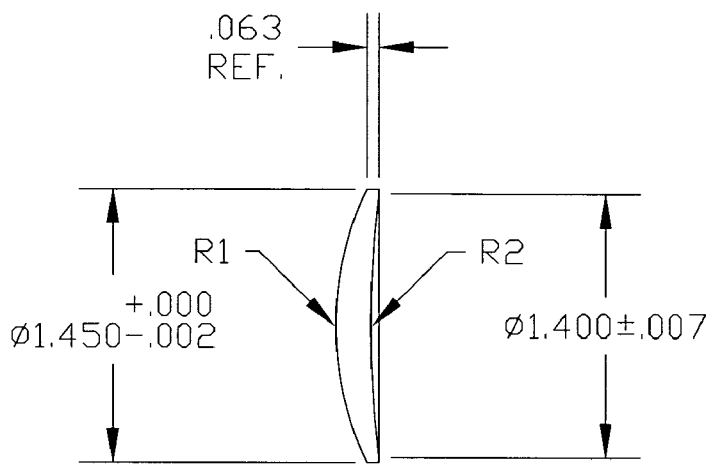
FIG. 27 shows a detailed side plan half cross sectional view with dimensional attributes of the preferred embodiment of element 3 of the lens shown in FIG. 23.
Figure 28:
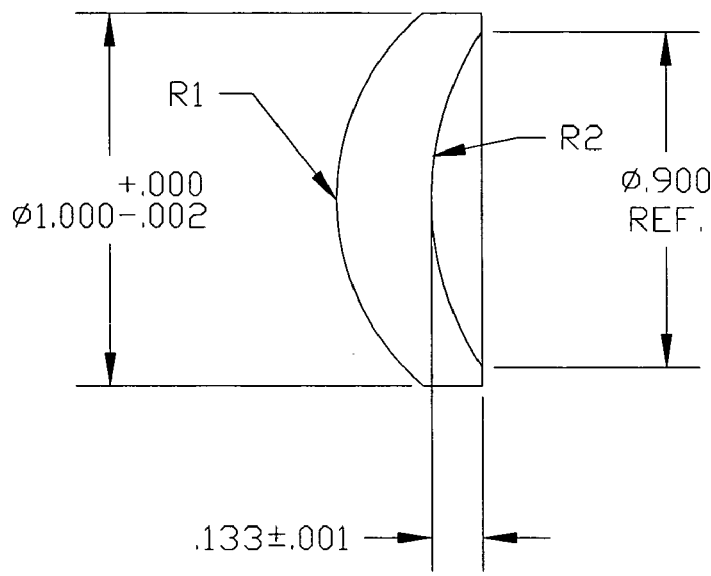
FIG. 28 shows a detailed side plan half cross sectional view with dimensional attributes of the preferred embodiment of element 4 of the lens shown in FIG. 23.
Figure 29:
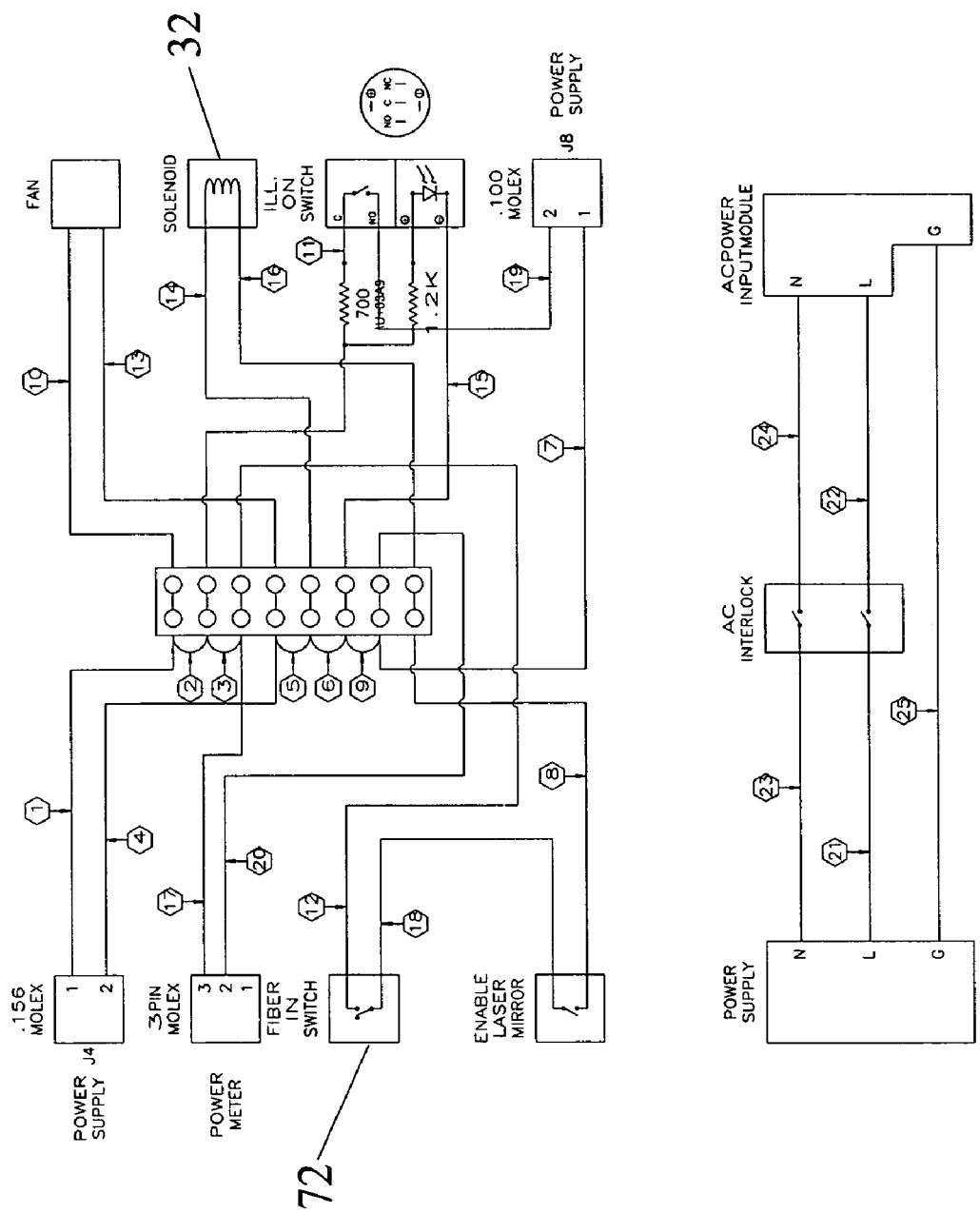
FIG. 29 shows an electrical schematic diagram of the coaxial illuminated laser endoscopic probe and active numerical aperture control apparatus.
Figure 30:
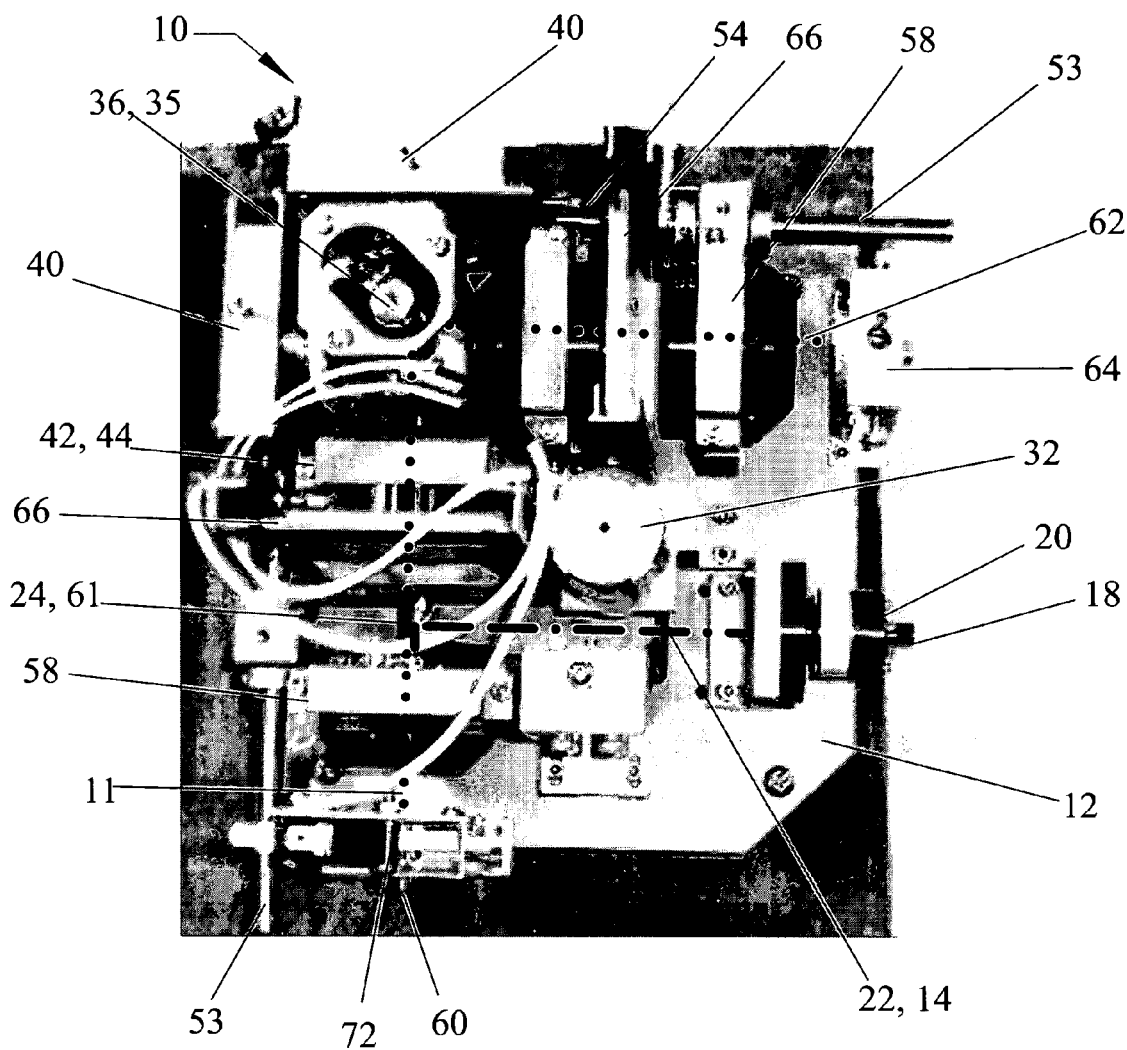
FIG. 30 shows a top perspective view in black and white photographic form of a preferred embodiment of the coaxial illuminated laser endoscopic probe and active numerical aperture control apparatus showing illumination and laser light paths without the phototoxicity card, power meter, and ferrule connectors.

Referring now to the drawings, there is shown in the Figures both preferred and alternate embodiments of the coaxial illuminated laser endoscopic probe and active numerical aperture control apparatus 10 also herein described as an illumination and laser source 10. There is provided a device 10 for providing non-coherent illumination light 11, 62 and coherent laser treatment light 14 through a single optical fiber 60 of the size typically used for laser treatment only in a safe, effective, and user friendly manner. The apparatus is especially suited for use during ophthalmic surgery.

The present art, in a preferred embodiment, utilizes a 75 watt xenon arc lamp 36 for its high luminance illumination (light density), greater than 6000° K color temperature, and greater than 95 color rendering index. A unique and useful feature is the very high luminance and small size plasma ball formed on the end of the lamp 36 cathode. If imaged correctly the plasma ball is bright enough to provide the required illumination input to a small fiber such as that used for laser treatment. The xenon arc lamp 36 further provides an extremely small point light source which allows for a smaller output illumination beam 37 diameter. Unique to the present lamp source is a mount 38 which allows for replacement of the lamp 36 and yet retains the location of the plasma ball of said source 36 precisely at a predetermined location within the optical center 35 of the apparatus.

A classic spherical reflector 40 and two lens 42, 58 light collection layout is utilized rather than other lower part count layouts, such as using an elliptical reflector or a combination of a parabolic reflector and lens. This technique allows maximum collection efficiency with a minimum of geometric aberration. The lamp 36 is located at the geometrical center 35 of the reflector 40 and at the focus (focal point) of the first lens 42. Light that is incident on the reflector 40 is reflected back to the lamp 36. This forms an upside down or inverted image of the source 36 coincidental to the source 36. The first lens 42 collimates light from the source 36 and the upside down or inverted image. The second lens 58 is located coaxial to the first lens 42 and focuses the light at its focal point. The output optical fiber 60 is located at the focal point of the second lens 58. The aforesaid reflectors 40 are preferably spherical rather than parabolic in order to reflect illumination light in the same form as sourced from the arc lamp 36.

Best form lenses 42, 58 (plano convex aspheric, facing each other) are used in the present art. It was discovered that chromatic aberrations, caused by the lenses, gave the output of the optical fiber 39, 60 either a yellow or blue cast. This is not a problem with other ophthalmic sources because the source is many times larger than the output optical fiber. A color corrected "f1" or possibly 0.5 numerical aperture lens set 42, 58 consisting of four elements was designed to be utilized for each lens. Each of the elements is coated with a MgF (magnesium fluoride) anti-reflective coating to minimize light losses, with other anti-reflective coatings or layers also utilizable. Use of the achromatic lens sets allows a high fidelity image of the illumination source 36 to be focused onto the end of the optical fiber 60, 64. That is, the multi-element lenses allow for a minimum of chromatic aberration. The aforesaid four element lens set is shown and specifically described in the Figures.

An additional separate illumination path 62 is possible with the present art. A 0.5 system numerical aperture or "f 1" lens is the greatest practical because of limitations to the numerical aperture of available optical fibers. This equates to 60 degrees full angle. When the spherical deflector 40 is considered, an additional 60 degrees is provided from the total of 360 degrees available. Consideration of the vertical rotation around the source 36 is impractical because of shadows caused by the lamp 36 electrodes. A total of 240 degrees of horizontal rotation around the lamp 36 are left unaccounted for. Allowing for optics mounts 44 does account for some additional amount. However, at least half of the illumination output is available. This leaves room for a second light path 62 located orthogonal to the first path 11 along with the second fiber output 64. No other conventional illumination light source incorporates multiple light paths from a single lamp, that is two independent collection systems for illumination light. The independent nature of the two paths 11, 62 allow different filtering and intensity control settings to the two outputs 39, 41.

Output dimming of the present art illumination system is accomplished by steering the first (collimating) or penultimate lens 42 in a fashion that does not change the lens 42 numerical aperture or introduce shadow artifacts into the beam 37. The lens set mount 44 has two halves 46 and a flat spring 52. The first part 48 is attached to the optics bench 12, the second part 50 holds the lens set 42, and the spring 52 connects the two 48, 50 together on one side. Pressure on the lens mount second part 50 causes the spring 52 to deflect and the lens 42 to move in a direction generally perpendicular to the optical axis. This results in motion or movement of the image across the face of the optical fiber 60, 64 whereby the peak illumination of the beam 37 is not centered on the optical fiber 60, 64 face during dimming. Due to the aforesaid, the reduction of the output light from the fiber 60, 64 without affecting the color (i.e. color temperature) or aperture of the output is achieved. In a preferred embodiment a shaft mounted cam 54 applies the pressure to the lens mount second part 50 and spring 52. A control knob 56 is attached to the other end of the shaft 53 and allows the user to select the desired illumination level by rotating the knob 56. This method is capable of providing at least 95% reduction in output illumination intensity. In a preferred embodiment, a shutter 57 is mounted upon the shaft 53 and is rotated across the illumination beam 37 in order to fully attenuate the output illumination intensity upon full rotation of said knob 56. Alternative embodiments may utilize other methods, including but not limited to electric or electronic drives, to rotate said shaft 53 instead of said knob 56.

A dichroic "hot" mirror filter 66 is placed in the collimated space 61 between the illumination lenses 42, 58. This provides both UV and IR filtering of the light. Brackets are attached to the hot mirror 66 mount to provide a means for additional user selectable filters. Positioning of the filters is critical because this is the only area where the light 11 is generally normal to the filter surface. Location of the filter 66 on the other sides of the lenses would cause the light to have many undesirable incidence angles (between 0 and 30 degrees). Variation in the incidence angle causes dichroic reflectors or filters to have a shift in their affect. If absorption filters are used, placement outside the collimated space 61 will cause an increase in reflective losses and heating problems.

The output optical fiber connector 98 is uniquely configured to provide the precise positioning required while reducing cost. A precise connector or mating end 116 is combined with an integral retention thread 130 to reduce parts cost and assembly time. An optional groove or recess 148 is placed on a second version of the connector to provide for sensing the difference between illumination only and laser compatible output fibers. Placement of a smooth diameter connector 74 into the output activates a switch 72 which will allow the laser power to be mixed. Either the lack of a connector 98 or the groove or recess 148 under the switch 72 will cause the switch 72 to not activate and the laser power will not be mixed in.

Regarding mixing of laser treatment energy or light 14, laser light 14 is delivered to the system via a preferably 50 micron optical fiber 16 or equivalent. The connector 18 on the laser end is configured to be compatible with the laser and to provide the necessary interface to signal to the laser that a fiber is connected. The laser and light source 10 end preferably uses an SMA 905 connector or equivalent to allow repeatable connections of the laser delivery fiber 16. Laser light exiting the delivery fiber is preferably collimated using a 16 mm focal length achromatic lens or equivalent 20, i.e. laser collimating lens, which can also be utilized to focus the collimated laser beam 22. The position of the fiber 16 is adjusted to be at the focal point of the lens 20. The input laser connector 18 and collimating lens 20 are located so that the collimated beam 22 is orthogonal to and intersects the center of the illumination axis 11 between the illumination lens sets 42, 58 (the collimated area for illumination light). If all safety requirements are met (i.e. laser output compatible fiber inserted and selection switch for laser output activated) a steering mirror 24 reflects the collimated laser light 22 into the center of the illumination axis 11. The steering mirror 24 is a first surface piano that is positioned at 45 degrees to the laser light 14 and is located in the center of the illumination axis 11 (when laser mode is active). A unique aspect of the present invention is that the thickness of the mirror 24 is shaped to appear as a circle when viewed along the illumination axis. Due to the 45 degree surface orientation, the shaping causes the mirror 24 surface to appear elliptical when viewed from a normal angle. The size of the mirror 24 is chosen to be minimally larger that the collimated laser beam 22. Placement of the steering mirror 24 in the center of the illumination axis 11 causes the light rays that would normally be there to be blocked and a shadow to appear in the center of the output light cone. The second illumination lens 58 focuses the laser light 14 reflected by the steering mirror 24 onto the end of the output fiber 60, 64. Because the length of the output optical fiber strand is relatively short, the incidence angle of light entering the input end is very nearly the same angle on the output end. This results in the output of the fiber strand having a cone of white light with a shadow in the center nearly filled with the laser aiming beam (treatment beam during treatment). That is, the laser provides an aiming beam, typically red, when not fully activated for treatment and a treatment beam, typically green, when fully activated. Without the shadow caused by the steering mirror 24 the aiming beam would be entirely washed out or imperceptible except at very low illumination levels.

Alternate embodiments may utilize more than one steering mirror 24 or place the steering mirror 24 outside of the illumination axis or illumination light path 11 and direct the laser light 14 through an aperture 158 in said spherical reflector 40 and thereafter through the arc lamp 36 plasma ball or through a dichroic reflector 160 or a reflector having an aperture 162. All of the aforesaid alternate embodiments place the laser light 14 within the collimated space 61 and utilize the second lens 58 for focus upon the output optical fiber 60. Moreover, all of the aforesaid alternate embodiments provide for a second light path 62 output as seen in the Figures.

The laser steering mirror 24 is mechanically mounted on a thin post 28 that holds it in place while minimizing the loss of illumination light 11. The post 28 is mechanically connected to a bracket 30 which is connected to a solenoid 32. The solenoid 32 causes the bracket 30 and also the steering mirror 24 to move into one of two positions. Position one is outside the collimated illumination and laser light. This position is used for no laser delivery and allows the illumination path to operate unaffected. Position two is with the steering mirror 24 located to reflect the laser light into the illumination path 11. Motion of the solenoid 32 and bracket 30 are controlled by a precision ball slide 34. Use of the slide 34 insures repeatable positioning of the mirror 24.

As described, unique to the present art is a coaxial laser and illumination path apparatus 10 which heretofore has not be available or utilized. Also unique to the present art is a highly efficient illumination system which utilizes spherical reflectors 40 and associated lenses 42, 58 to capture a maximum light output and also provide a twin path illumination light output from a single lamp source in order to feed fibers of diameter less than 500 microns. Further unique to the present art is a laser or steering mirror 24 having a solenoid 32 selectability which provides an aiming hole within the illumination path 11 for laser placement. Still further unique to the present art is an illumination arc lamp 36 system having an extremely small point light source 36 which allows for an extremely small illumination focus size or numerical aperture output. Also unique to the present art is an arc lamp 36 mount 38 which precisely and interchangeably places the plasma ball of the arc lamp 36 at the focus or optical center 35 of the optics system. Also unique to the present art is a unique dimming mechanism which moves the focal point of an output dimming or first lens 42 in order to provide dimming without introducing artifacts, chromatic aberrations, or change of color temperature. Also unique to the present art is a capability of connection with existing conventional laser light sources whereby laser treatment and illumination are both provided at an output of the present art apparatus 10. The optical system of the present apparatus 10 is uniquely capable of accepting the input cone angles of the illumination 33 and laser light 15 placed at the output optical fiber 60 and substantially reproducing said cone angles at the output of the optical fiber, typically where the endoscopic probe is located, with any aberrations caused by the optical fiber itself.

Further alternate embodiments of the present art apparatus 10 may utilize parabolic reflectors instead of spherical reflectors in order to collimate the illumination source 36. This technique would eliminate the need for the first collimating lens 42 and allow transmission of the laser beam 22 through an aperture within the parabolic reflector or via a steering mirror 24 within the collimated space 61. Still further alternate embodiments may utilize an elliptical reflector having two focal points whereby the illumination source 36 is placed at the first focal point and the output fiber 60 is placed at the second focal point with the laser beam 22 introduced through an aperture within the elliptical reflector or via a steering mirror 24 between the illumination source 36 and the output fiber This latter alternate embodiment requires focusing the laser beam 22 onto the output fiber 60 via a lens placed within the laser beam path 22 prior to the output fiber 60 yet allows elimination of both the first collimating lens 42 and the second focusing lens 58.

Some of the variables which determine the phototoxicity risk level during vitreoretinal surgery include the spectral and power characteristics of the light source used, the type and size of the endoilluminator probe, the length or duration of the surgical procedure, and the area (size) of the illuminated tissues. In each case the surgeon must make a risk-benefit judgement about the intensity of light to be used. Use of insufficient intensity may result in inadequate visualization and adverse effects more serious than a retinal photic injury. Currently, the calculation of the exposure time required to reach a point of injury is a tedious chore involving the numerical integration of the spectral power density function of the light source 36 with a hazard function (see ISO 15752), and specific knowledge of the surgical illumination area and endoilluminator characteristics.

The present art invention further represents a novel apparatus and method for providing the ophthalmic surgeon with graphical photoxicity risk information in a clear and easy to understand manner. In a preferred embodiment, an inexpensive photoxicity risk card 76 is removably attached to the control panel of the surgical illumination and laser light source 10. Preferably, the present art card 76 is attached in close proximity to the light intensity control knob 56 in order to show the relationship between the output intensity of the light source and the likelihood of photic injury. The card 76 is preferably included with each endoilluminator instrument, i.e. optical fiber, that is calibrated to represent the phototoxic performance of that instrument type when used with a particular type of light source. The graphical representation 78 on the card 76 acts as a guide for adjustment of the output intensity of the source 10 in relationship to an accepted standard, that is such as the "Millennium" from Bausch and Lomb®. In this way the spectral and power characteristics of the various elements involved in delivering light to the eye are integrated into a single and easily manageable variable. This greatly reduces the complexity of judging the best intensity to use in a given situation. Alternative embodiment graphical representations 78 could present other information regarding the light output such as lumen output (a unit that is weighted by the photopic response of the eye). Other representations could present threshold information when used with special dyes or colored light filters.

A preferred embodiment of the invention comprises a card 76 that is die-cut from white chipboard stock that is approximately the weight of a business card. The shape of the card 76 is generally square with a slot 90 removed from one side to enable the card 76 to be placed behind the intensity control knob 56 of the illumination and laser source 10 while providing clearance for the control shaft 53 which is turned by said knob 56. In a preferred embodiment, four location pins 92 are attached to the front panel of the illumination and laser source 10 enclosure. The pins 92 provide boundaries for card 76 location and tend to inhibit rotation of the card 76 with the control knob.

In a preferred embodiment, onto the face of the card is printed a circular shaped scale 84 that has different color bands 86 representing the phototoxicity risk at a given intensity level, for example green, yellow, and red. The control knob 56 has an indication line that points to the current output intensity level and concurrent phototoxicity risk associated with the probe being used. Unique to the present art is the ability of the card 76 to indicate output intensity at the optical fiber output. The card 76 is meant to be disposed of after a single use and replaced with a new one provided with each optical fiber instrument. In this manner the output of the light source 10 is recalibrated each time it is used. The calibrated unit type may vary with different instrument styles to provide the surgeon with the most pertinent information possible.

As aforesaid the card 76 provides a known point of reference relative to the prior art illumination devices. For example, if the surgeon maintains the knob 56 indicator line within the green color band, he or she will understand that the light intensity output is within the safe intensity of the prior art illuminators such as the "Millennium" from Bausch and Lomb®. This control phenomena is especially useful when utilizing more powerful illumination sources 10 such as described herein. That is, the surgeon must have a prior art point of reference when utilizing more powerful and modern illumination systems such as the present art. The art of the present invention may further provide several bands which do not provide a reference to the prior art but instead indicate phototoxicity levels or light intensity levels directly to the surgeon.

Unique to the present art is the ability of the manufacturer of the optical fiber to provide a phototoxicity risk card 76 which accounts for attenuation and spectral absorption within the optical fiber provided with said card 76. Thus for example, if an optical fiber is highly attenuating, the card may indicate that the surgeon must turn the intensity control knob 56 to a higher level in order to obtain an equivalency to one or more of the aforesaid prior art illuminators or to achieve a desired photo-illumination output.

The art of the present invention also comprises a ferrule or connector 98 having an internal bore 102, preferably stepped 104, which is substantially parallel with the lengthwise axis 100 of the ferrule body 98. The aforesaid bore 102 allows for placement and bonding or potting of an optical fiber within and through said ferrule body 98. Externally, said ferrule body 98 is also stepped 112, 148 in a unique form in order to optimally function as described herein.

In a preferred embodiment, the ferrule body 98 has an external end 114 and a mating end 116 and externally comprises a substantially cylindrical head 118 of a first diameter 120 having a first end 122 and a second end 123, said first end 122 co-located with said external end 114. Said ferrule body 98 further externally comprises a lip 124 of greater diameter than said head 118 and having a first side 126 and a second side 128 with said first side 126 mounted with said second end 123 of said head 118. A threaded portion 130 of preferably smaller diameter than said head 118 is attached with and extends from said lip 124 second side 128. In a preferred embodiment, said threaded portion 130 first comprises an 8-32 UNC thread with a first end 132 and second end 134, said first end 132 connected with said second side 128 of said lip 124. Also in a preferred embodiment, said threaded portion 130 has a groove 136 of approximately 0.030 inch at said first end 132 with approximately 0.090 inch of said thread 130 thereafter following and another approximately 0.030 inch groove 136 following said thread 130 at said second end 134. Externally the ferrule body 98 also has an alignment barrel 138 having a first 140 and second 142 end following said threaded portion 130, said first end 140 attached with said threaded portion 130. The second end 142 of said alignment barrel 138 is co-located with said mating end 116 of said ferrule body 98. Also, said second end 142 of said alignment barrel 138 contains an orifice 144 of substantially equivalent or slightly greater diameter as the optical fiber mounted within said stepped bore 102. Said orifice 144 is interconnected with said internal stepped bore 102. In an embodiment of the present art, said orifice is approximately 0.011 inch in diameter and 0.025 inch in length. Also in a preferred embodiment, said alignment barrel 138 has a chamfer 146 at the circumference of said second end 142. Preferably said chamfer 146 is of approximately 45 degree angle and 0.015 inch in length. Alternative embodiments may utilize chamfers of different angles or shapes or forego use of a chamfer altogether.

The alignment barrel 138 of the present art is uniquely shaped within the embodiments to indicate whether laser light or illumination light should be applied to the optical fiber. In a preferred embodiment of the laser ferrule, the alignment barrel is of uniform diameter, approximately 0.118 diameter, which indicates to the source 36 that laser light or energy is desired. In a first alternative embodiment or illumination ferrule, the alignment barrel contains a recess 148 located approximately 0.075 inch from said barrel 138 second end 142 and extending approximately 0.268 inch from said second end 142. When utilized, the illumination and laser source 10 detects this recess and determines that illumination light and not laser light is desired. Further alternative embodiments may utilize the aforesaid recess 148 embodiment for laser light and the uniform barrel diameter for illumination light.

Internally said stepped bore 102 first comprises a first larger bore substantially within said head portion which is of approximately 0.098 inch diameter and extends substantially the length of said head. A second intermediate bore of approximately 0.063 inch diameter extends from said first larger bore to said orifice 144 within said threaded portion 130 and said alignment barrel 138. Also in a preferred embodiment, the orifice 144 length is approximately 0.025 inch. Alternative embodiments may utilize first and second bores and orifices having a plurality of diameter and length sizes provided that the diameter portions are smaller than the ferrule external portions within which each is located.

When assembled with an optical fiber, the optical fiber extends through said bore 102 and orifice 144 and terminates substantially flush with said ferrule body 98 mating end 116 or second end 142 of said alignment barrel 138. Preferably said optical fiber is held within said bore 102 via potting or adhesive compounds surrounding said fiber and attaching with said bore 102 of the ferrule 98.

In a preferred embodiment, the external head 118 diameter is approximately 0.234 inch with a length of approximately 0.375 inch. The lip 124 external diameter is approximately 0.312 inch with a thickness of approximately 0.025 inch. Also, said alignment barrel 138 is approximately 0.118 inch in diameter and 0.380 inch in length.

Where provided, dimensions, geometrical attributes, and thread sizes are for preferred embodiment informational and enablement purposes. Alternative embodiments may utilize a plurality of variations of the aforesaid without departing from the scope and spirit of the present invention. This is especially true as relating to said head 118, lip 124, and threaded portion 130. Said lip 124 may be integrated as part of the head 118 or removed completely. Also, the position, location, and type of threaded portion 130 may vary. Said threaded portion 130 may not utilize said grooves 136, utilize grooves of a shorter or longer length, or have said head 118 and lip 124 diameters sized substantially the same as or smaller than the outside diameter of said threads 130. The art of the present invention may be manufactured from a plurality of materials, including but not limited to metals, plastics, ceramics, or composites.

Unique to the present invention is the integral inclusion of a laser power meter 150 having a sensor 152, a power display 154, and associated control circuitry 156. The power meter 150 allows a surgeon to place the endoscopic fiber optic probe onto said sensor 152, energize the laser through the illumination and laser source 10 and measure the laser power output as seen on said display 154. Inclusion of the aforesaid is especially useful due to variations in optical fibers or to account for attenuation through the illumination and laser source 10. By utilizing the power meter 150, the surgeon has complete knowledge of the laser power transmitted to the surgical site. Alternative embodiments may utilize said power meter 150 for measurement of the output illumination 37 intensity as well as the laser light 14 power.

In operation, the surgeon connects a laser light source via optical fiber to the input laser connector 18 on the apparatus 10. The surgeon thereafter connects a ferrule connector 98 with an integral optical fiber connected with an endoscopic probe at the first output 39 or for illumination only at said second output 64. If said ferrule connector 98 at said first output 39 does not have the aforedescribed recess 148, the apparatus 10 will allow the steering mirror 24 to position within the illumination light path 11 and further allow transmission of laser light. If the surgeon desires to measure laser power output, he or she places the output end of the endoscopic probe onto said sensor 152 and upon full laser activation, reads the laser power output on the display 154. If the apparatus 10 is powered, the surgeon proceeds to illuminate the tissues of concern with a cone of white illumination light having a shadow where the laser beam will be placed and a typically red laser aiming beam within said shadow. Upon full activation of laser power, a typically green treatment laser beam replaces said typically red aiming beam to treat the tissues of concern. All of the aforesaid illumination and treatment may be achieved with a single incision and through a single optical fiber of smaller diameter than prior art sources.

Those skilled in the art will appreciate that a coaxial illuminated laser endoscopic probe and active numerical aperture control apparatus 10 (illumination and laser source) and method of use such has been shown and described. The apparatus and method of use allows for simultaneous transmission of illumination and laser treatment light through a single optical fiber of a size which is typically utilized for laser treatment light only. The apparatus and method further provides control of the angular light output from the endoscopic probe attached with said optical fiber. The apparatus also provides for distinct and separate illumination without utilization of the treatment laser while providing complete intensity control of said illumination. Those skilled in the art will appreciate that a medical light intensity phototoxicity control or risk card 76 has also been shown and described for use with the present art. Said phototoxicity risk card 76 is especially useful for quick and easy determination of illumination intensity output from a specific type of optical fiber or higher power source such as the present art. Those skilled in the art will appreciate that a photon illumination and laser ferrule connector 98 has also been shown and described. Said ferrule 98 is especially useful for quick and positive connection of an optical fiber to a laser or illumination source 10 as herein described and further allows said source 10 to distinguish the optical fiber type or use, that is for illumination or medical laser application. The present art device is useful during surgery and especially ophthalmic surgery. Also, those skilled in the art will appreciate the integral inclusion of a laser optical fiber output power meter.

Having described the invention in detail, those skilled in the art will appreciate that modifications may be made of the invention without departing from its spirit. Therefore, it is not intended that the scope of the invention be limited to the specific embodiments illustrated and described. Rather it is intended that the scope of this invention be determined by the appended claims and their equivalents.

What is claimed is:

1. An illumination and laser source comprising:
an illumination source having an output of surgically useful visible broad spectrum illumination light and an illumination focus spot of a size sufficiently small to be substantially focused upon a substantially single output fiber of 500 microns or less, said focus spot size substantially within an optical center; and
a laser light source having an output of laser light; and
means for mixing said illumination light and said laser light and focusing with a first and second incidence angle respectively both said illumination light and said laser light onto said single output optical fiber whereby said laser light and said illumination light are transmitted through said single output optical fiber and exit an output of said optical fiber without a washing out of said laser light by said illumination light and with said light incidence angles substantially similar at said output; and
said illumination light at said output of said optical fiber capable of being dimmed.

2. The illumination and laser source as set forth in claim 1 whereby said means for mixing said illumination light output and said laser light output further comprises:
a means for substantially preserving an illumination light cone having a first cone angle from said illumination light output and a laser light cone having a second cone angle from said laser light output at an output of said optical fiber.

3. The illumination and laser source as set forth in claim 2 whereby:
said illumination light cone has a shadow within which is located said laser light at said output of said optical fiber whereby one or more tissues of concern are illuminatable and said shadow appears on said tissues where said laser light provides a treatment.

4. The illumination and laser source as set forth in claim 1 whereby said means for mixing said illumination light and said laser light comprises:
means for collimating said laser light into a collimated laser light beam; and
means for collimating said illumination light into a collimated illumination light beam; and
means for combining said collimated beams together; and
means for focusing said collimated beams onto said single output optical fiber; and
said output of said optical fiber capable of illuminating one or more tissues with said illumination light and selectively capable of treating one or more tissues with said laser light.

5. The illumination and laser source as set forth in claim 4 whereby:

said means for collimating said laser light into a collimated laser light beam comprises a laser collimating lens; and said means for collimating said illumination light into a collimated illumination light beam comprises a first collimating lens; and said means for combining said collimated beams together comprises a steering mirror which reflects said collimated laser light from said laser collimating lens into an illumination axis of said collimated illumination light; and said means for focusing said collimated beams onto said output optical fiber comprises a second focusing lens.

6. The illumination and laser source as set forth in claim 5 whereby:

said means for combining said collimated beams together comprises said steering mirror positioned at substantially 45 degrees to said collimated laser light and substantially in a center of said illumination axis and shaped to substantially appear as a circle when viewed along said illumination axis and which positions said collimated laser light with said collimated illumination light.

7. The illumination and laser source as set forth in claim 4 further comprising:

one or more illumination light filters placed within said collimated illumination light beam and at least capable of filtering IR light.

8. The illumination and laser source as set forth in claim 7 whereby:

said filters are placed within said collimated illumination light substantially normal to said illumination light beam.

9. The illumination and laser source as set forth in claim 1 further comprising:

a connector means for connecting said output optical fiber, said connector means providing an indication whether said output optical fiber is designed, best suited, or desired for said illumination light or said laser light or both said illumination light and said laser light; and a sensing means capable of sensing said indication of said connector means and activating said mixing of said laser light with said illumination light if said output optical fiber is designed, best suited, or desired for said illumination light or said laser light or both said illumination light and said laser light.

10. The illumination and laser source as set forth in claim 1 whereby:

said illumination light at said output of said optical fiber capable of being dimmed comprises means for dimming said illumination light having a control without substantially affecting the spectral characteristics of said illumination light and without introducing shadow artifacts via movement of an illumination image across a face of said output optical fiber.

11. The illumination and laser source as set forth in claim 10 whereby said means for dimming said illumination light comprises:

a steerable lens capable of moving said image of said illumination source across said face of said output optical fiber.

12. The illumination and laser source as set forth in claim 1 further comprising:

a second illumination light path comprising said illumination light available from said illumination light source but not used by said means for mixing said illumination light and said laser light; and means for focusing said second illumination light path onto a second output optical fiber whereby said laser light is omitted from said illumination light in said second illumination light path and whereby said laser light and said illumination light transmitted through said substantially single output optical fiber are unaffected by said second illumination light path.

13. The illumination source as set forth in claim 1 whereby:

said illumination source comprises an arc lamp having a mount which allows for replacement of said arc lamp and yet retains a location of a plasma ball of said illumination source precisely at a predetermined location within an optical center.

14. An illumination and laser source comprising:

an illumination source having an output of surgically useful broad spectrum illumination light; and a laser light source having an output of laser light; and means for mixing said illumination light and said laser light and focusing both said illumination light and said laser light onto a single output optical fiber whereby said laser light and said illumination light are transmitted through said single output optical fiber; and means for dimming said illumination light having a control without substantially affecting the spectral characteristics of said illumination light; and a photoxicity risk card placable near or onto said control and capable of indicating a safe or known output intensity of said illumination light.

15. An illumination and laser source comprising:

an illumination source having an output of surgically useful visible broad spectrum illumination light and an illumination focus spot of a size sufficiently small to be substantially focused upon a substantially single output optical fiber of 500 microns or less, a first lens capable of collimating a portion of said illumination light into a collimated illumination light path; and a laser light source having an output of laser light; and said laser light collimated and positioned to form a collimated laser beam within said collimated illumination light path; and a second lens capable of focusing said collimated illumination light and said collimated laser beam onto said substantially single optical fiber; and said illumination light at said output of said optical fiber capable of being dimmed.

16. The illumination and laser source as set forth in claim 15 further comprising:

a laser collimating lens capable of collimating said laser light; and a steering mirror within an axis of said collimated illumination light path and reflecting said collimated laser beam whereby said collimated laser beam is within said collimated illumination light path.

17. The illumination and laser source as set forth in claim 16 whereby:

said collimated laser beam within said collimated illumination light is substantially parallel with said illumination light.

18. The illumination and laser source as set forth in claim 15 whereby:

said steering mirror provides a shadow which does not wash out said laser beam within said collimated illumination light path where said collimated laser beam is placed and an output of said optical fiber is capable of illuminating one or more tissues of concern and said shadow appears on said tissues where said laser beam will be placed for treatment.

19. The illumination and laser source as set forth in claim 15 further comprising:
a dimming mechanism comprising a mount on said first lens capable of steering said first lens in a direction substantially perpendicular to an optical axis of said collimated illumination light path whereby a lens numerical aperture of said first lens is not substantially changed.

20. The illumination source as set forth in claim 15 whereby:
said illumination source comprises an arc lamp having a mount which allows for replacement of said arc lamp and yet retains a location of a plasma ball of said illumination source precisely at a predetermined location within an optical center.

21. An illumination and laser source comprising:
an illumination source having an output of illumination light,
a first lens capable of collimating a portion of said illumination light into a collimated illumination light path; and
a laser light source having an output of laser light; and
said laser light collimated to form a collimated laser beam within said collimated illumination light path; and
a second lens capable of focusing said collimated illumination light and said collimated laser beam onto an optical fiber; and
a laser collimating lens capable of collimating said laser light; and
a steering mirror capable of reflecting said collimated laser beam whereby said collimated laser beam is within said collimated illumination light path; and
one or more spherical reflectors having a geometrical center; and
said illumination source located at said geometrical center and at a focal point of said first lens.

22. An illumination and laser source comprising:
an illumination source having an output of illumination light,
a first lens capable of collimating a portion of said illumination light into a collimated illumination light path; and
a laser light source having an output of laser light; and
said laser light collimated to form a collimated laser beam within said collimated illumination light path; and
a second lens capable of focusing said collimated illumination light and said collimated laser beam onto an optical fiber; and
one or more spherical reflectors having a geometrical center; and
said illumination source located at said geometrical center and at a focal point of said first lens.

23. An illumination and laser source comprising:
an illumination source having an output of illumination light,
a first lens capable of collimating a portion of said illumination light into a collimated illumination light path; and a laser light source having an output of laser light; and
said laser light collimated to form a collimated laser beam within said collimated illumination light path; and
a second lens capable of focusing said collimated illumination light and said collimated laser beam onto an optical fiber; and
a dimming mechanism comprising a mount on said first lens capable of steering said first lens comprising a first part attached with an optics bench and a second part holding said first lens, said first part and second part attached with a spring whereby a pressure on said second part causes said spring to deflect and said first lens to move.

24. The illumination and laser source as set forth in claim 23 said dimming mechanism mount further comprising:
a cam capable of applying said pressure to said second part.

25. An illumination and laser source comprising:
an illumination source having an output of illumination light,
a first lens capable of collimating and steering a portion of said illumination light into a collimated illumination light path, said first lens steering providing a dimming of said illumination light; and
a laser light source having an output of laser light; and
said laser light collimated to form a collimated laser beam within said collimated illumination light path; and
a second lens capable of focusing said collimated illumination light and said collimated laser beam onto an optical fiber; and
a connector mounted with said optical fiber and capable of indicating whether said laser light or said illumination light or both should transmit through said optical fiber; and
a phototoxicity risk card capable of providing a representation of illumination risks during dimming.

26. An illumination and laser source comprising:
an illumination source emanating surgically useful broad spectrum illumination light substantially focused onto a single output optical fiber of 300 microns diameter or less thereby forming an illumination spot size; and
said illumination spot size of sufficient intensity to provide surgically useful illumination through said optical fiber during a surgical procedure; and
a laser treatment light source providing focused laser treatment light upon said output optical fiber whereby both said laser treatment light and said illumination light transmit through said optical fiber and emit with said laser treatment light substantially centered within said illumination light; and
an illumination light dimming mechanism capable of dimming said illumination light emitted from said optical fiber without affecting said laser treatment light or introducing shadow artifacts into said illumination light.

* * * * *